(12) United States Patent
Chivukula et al.

(10) Patent No.: US 10,968,248 B2
(45) Date of Patent: Apr. 6, 2021

(54) TRINUCLEOTIDE MRNA CAP ANALOGS

(71) Applicant: c/o Arcturus Therapeutics, Inc., San Diego, CA (US)

(72) Inventors: Padmanabh Chivukula, San Diego, CA (US); Steven P. Tanis, Carlsbad, CA (US); Joseph E. Payne, San Diego, CA (US)

(73) Assignee: Arcturus, Inc., San Diego, CA (US)

( * ) Notice: Subject to any disclaimer, the term of this patent is extended or adjusted under 35 U.S.C. 154(b) by 0 days.

(21) Appl. No.: 16/600,336

(22) Filed: Oct. 11, 2019

(65) Prior Publication Data

US 2020/0040026 A1 Feb. 6, 2020

Related U.S. Application Data

(63) Continuation of application No. 15/788,742, filed on Oct. 19, 2017, now Pat. No. 10,487,105.

(60) Provisional application No. 62/410,325, filed on Oct. 19, 2016.

(51) Int. Cl.
| | |
|---|---|
| *C07H 21/00* | (2006.01) |
| *C07H 19/16* | (2006.01) |
| *C07H 19/20* | (2006.01) |
| *C07H 19/207* | (2006.01) |
| *C07H 21/02* | (2006.01) |
| *A61K 31/7125* | (2006.01) |

(52) U.S. Cl.
CPC ......... *C07H 19/16* (2013.01); *A61K 31/7125* (2013.01); *C07H 19/20* (2013.01); *C07H 19/207* (2013.01); *C07H 21/02* (2013.01)

(58) Field of Classification Search
None
See application file for complete search history.

(56) References Cited

U.S. PATENT DOCUMENTS

| | | | |
|---|---|---|---|
| 7,074,596 | B2 | 7/2006 | Darzynkiewicz et al. |
| 7,101,993 | B1 | 9/2006 | Cook et al. |
| 9,051,570 | B2 | 6/2015 | Wengel |
| 9,297,009 | B2 | 3/2016 | Wengel |
| 2014/0378538 | A1 | 12/2014 | Bancel |

FOREIGN PATENT DOCUMENTS

| | | |
|---|---|---|
| WO | WO 1999/014226 | 3/1999 |
| WO | WO 2009/124238 | 10/2009 |
| WO | WO 2013/130161 | 9/2013 |
| WO | WO 2017/053297 | 3/2017 |
| WO | WO 2017/066781 | 4/2017 |
| WO | WO 2017/066782 | 4/2017 |
| WO | WO 2017/066789 | 4/2017 |
| WO | WO 2017/066791 | 4/2017 |
| WO | WO 2017/066793 | 4/2017 |
| WO | WO 2017/066797 | 4/2017 |

OTHER PUBLICATIONS

Darzynkiewicz et al. Biochemistry (1987), vol. 26, pp. 4372-4380.*
Ishikawa, et al. Nucleic Acids Symposium Series No. 53, 2009, pp. 129-130.
Belanger, et al. Journal of Biological Chemistry, 2010, pp. 33037-33044, vol. 285.
Lewdorowicz, et al., Synthesis of Leishmania CAP-4 Intermediates, CAP-2 and CAP-3, Nucleosides, Nucleotides, and Nucleic Acids, 2007, pp. 1339-1348, vol. 26.
Smith, et al., A Unique Class of Compound, Guanosine-Nucleoside Tetraphosphate G(5')pppp(5')N, Synthesized during the in Vitro Transcription of Cytoplasmic Polyhedrosis Virus of Bombyx mori, The Journal of Biological Chemistry, Jan. 1982, pp. 485-494, vol. 257, No. 1.
Tahara, et al., Effect of Eukaryotic Initiation Factor 4F on AUG Selection in a Bicistronic Mrna, The Journal of Biological Chemistry, Feb. 1991, pp. 3594-3601, vol. 266, No. 6.
Yoffe, et al. Binding Specificities and Potential Roles of Isoforms of Eukaryotic Initiation Factor 4E in Leishmania, Eukaryotic Cell, Dec. 2006, pp. 1969-1979, vol. 5 No. 12.
Ishikawa, et al., Preparation of eukaryotic mRNA having differently methylated adenosine at the 5'-terminus and the effect of the methyl group in translation, Nucleic Acids Symposium Series No. 53, Sep. 2009, pp. 129-130.
Peyrane, et al., High-yield production of short GpppA- and 7MeGpppA-capped RNAs and HPLC-monitoring of methyltransfer reactions at the guanine-N7 and adenosine-2'O positions, Nucleic Acids Research, 2007, 11 pages, vol. 35, No. 4.
Bhattarai, et al., a,B-Methylene-ADP (AOPCP) derivatives and analogs: development of potent and selective ecto-5'-nucleotidase (CD73) inhibitors, Journal of Medicinal Chemistry, 2015, 25 pages, vol. 58, No. 15.
Belanger, et al., Characterization of hMTr1, a Human Cap12'-O-Ribose Methyltransferase, The Journal of Biological Chemistry, Oct. 2010, pp. 33037-33044, vol. 285, No. 43.
Sommer, Prediction of the Electrophoretic Motilities of Nucleotides on Neutral Paper, Analytical Biochemistry, 1979, pp. 8-12, vol. 98A.
Canaani, et al. Sequence heterogeneity at the 5' termini of late simian virus 40 19S and 16S mRNAs, Proc. Natl. Acad. Sci., Jul. 1979, pp. 3078-3082, vol. 76, No. 7.

(Continued)

*Primary Examiner* — Patrick T Lewis
(74) *Attorney, Agent, or Firm* — Mintz Levin Cohn Ferris Glovsky & Popeo PC

(57) ABSTRACT

What is described is a trinucleotide cap analog comprising $m^7G(5')p_3-N_1pN_2$ for increased efficiency of in vitro transcription of $m7G(5')p_3$-RNA, wherein $m^7G$ is $N^7$-methyl-guanosine or analog, $(5')p_3$ is a 5',5'-triphosphate bridge, and $N_1$ or $N_2$ or both ribonucleotide analogs linked to each other by a phosphate, p, and wherein the trinucleotide cap analog increases the efficiency of in vitro transcription.

18 Claims, 16 Drawing Sheets

(56) References Cited

OTHER PUBLICATIONS

Kim, et al., Spatial Configuration of the Bizarre 5' Terminus of Mammalian mRNA1, Journal of the American Chemical Society, 1978, pp. 1571-1590.
European Patent Office, International Search Report and Written Opinion for PCT/US2017/057481, dated Mar. 26, 2018, 19 pages.

* cited by examiner

TRINUCLEOTIDE MRNA CAP ANALOGS

CROSS REFERENCE TO RELATED APPLICATIONS

This application is a continuation of U.S. patent application Ser. No. 15/788,742, filed Oct. 19, 2017, which claims the benefit of U.S. Provisional Application No. 62/410,325, filed Oct. 19, 2016, each of which is incorporated by reference herein in its entirety.

TECHNICAL FIELD

The description herein is directed to trinucleotide cap analogs for improved in vitro mRNA synthesis and translation of $m^7G(5')p_3$-RNA.

BACKGROUND

Eukaryotic mRNAs have a cap structure at their 5'-termini. The cap consists of 7-methyl guanosine ($m^7G$) and a triphosphate bridge, ppp ($p_3$), linking the 5'OH of $m^7G$ to the 5'OH of the 5'-terminal nucleotide, N, denoted $m^7G(5')pppN$ ($m^7G(5')p_3N$). In eukaryotic cells, the cap structure participates in assembly of the translation initiation complex by binding eukaryotic translation initiation factor 4E (eIF-4E).

Although $m^7G(5')p_3$ can be used to initiate transcription with T7 or SP6 DNA-dependent RNA polymerase in vitro, it has the disadvantage of having to compete with guanine nucleotide (G) as the initiating nucleophile for transcriptional elongation. As a result of this competition, less than half of mRNA produced in vitro have a cap structure at their 5' termini.

Dinucleotide $m^7G(5')p_3(5')G$, in which a guanine nucleotide (G) is linked via its 5'OH to the triphosphate bridge, has been used as an initiator of transcription. This dinucleotide has the disadvantage that the 3'-OH of either the $m^7G$ or G moiety serves as the initiating nucleophile for transcriptional elongation that results in synthesis of two isomeric RNAs of the form $m^7G(5')p_3G(pN)_n$ and $G(5')p_37G(pN)_n$, with one third to one half of the caps oriented in the reverse direction, depending upon the ionic conditions of the transcription reaction. Further improvement of the orientation of the cap during in vitro transcription is possible using cap analogues that replace the 3'-OH group with hydrogen or —$OCH_3$ (U.S. Pat. No. 7,074,596; Kore, 2006, *Nucleotides, Nucleotides, and Nucleic Acids,* 25: 307-14, and Kore, 2006, *Nucleotides, Nucleotides, and Nucleic Acids,* 25: 337-40).

Dinucleotide GG cap analogs $m^7G(5')p_3G$ and 3'-OMe-$m^7G(5')p_3G$ (ARCA) are sold commercially by TriLink BioTechnology, MilliporeSigma, ThermoFisher Scientific, and New England BioLabs Inc. 3'-OMe-$m^7G(5')p_3G$ (ARCA) is incorporated during transcription without reversal to $G(5')p_3 m^7G$.

Trinucleotide cap analogs were disclosed by Ishikawa, 2009, *Nucleic Acid Symp. Ser.,* 53:129-30. These are as follows:
  $m^7G(5')p_3ApG$, corresponding to the terminal trinucleotide of plant RNA;
  $m^7G(5')p_3AmpG$ (Am is adenine with a 2'OMe-ribose), corresponding to the terminal trinucleotide of animal RNA;
  $m^7G(5')p_3m^6AmpG$ ($m^6A$ is $N^6$-methyladenine), corresponding to the terminal trinucleotide of mammal RNA; and
  $m^7G(5')p_3m^6ApG$, an unnatural trinucleotide.

Ishikawa discloses that translational efficiency in a rabbit reticulocyte lysate system is greatest with mRNA transcribed with an animal-type, followed by a mammalian-type, the unnatural, and the plant-type cap structures, respectively, and that $G(5')p_3Ampm^7G$-RNA, a result of transcribing in a reverse orientation, was not obtained. Id.

In view of the disclosure of these publications, there remains a need to identify modified cap structures that improve the efficiency of in vitro transcription.

SUMMARY

Disclosed herein is a trinucleotide cap analog consisting of $m^7G(5')p_3$-$N_1pN_2$, in which a $m^7G$ ribonucleotide is linked at its 5'-OH to a triphosphate bridge ($p_3$), wherein the triphosphate bridge is linked to a 5'-OH of ribonucleotide $N_1$, wherein $N_1$ is linked via its 3'-OH to a phosphate, wherein the phosphate is linked to a 5'-OH of a second ribonucleotide $N_2$, and wherein $N_1$ or $N_2$ or both consist of a modified base or a modified ribose. The trinucleotide cap analogs described herein provide improved transcriptional efficiency for in vitro synthesis of capped mRNA, $m^7G(5')p_3$-RNA.

In one aspect, disclosed herein is a compound of formula $m^7G(5')p_3(5')N_1pN_2$, wherein $m^7G$ is a ribonucleotide consisting of $N^7$-methylguanine and a ribose or a modified ribose wherein one or both of the ribose 2' or 3' carbons has a fluoro or a C1-C6 alkoxy substituent; $(5')p_3(5')$ is a 5' to 5' triphosphate linkage, wherein the triphosphate linkage may be substituted with one or more phosphorothioate groups; $N_1$ comprises a seco (UNA) ribose optionally substituted at the 2' or 3' carbons with one or more fluoro or C1-C6 alkoxy substituents, and a base selected from the group consisting of adenine, uridine, guanine, cytosine, $N^6$-methyladenine, $N^1$-methyladenine, pseudouracil, $N^1$-methylpseudouracil, 5-iodouracil, 4-thiouracil, 2-thiouracil, 5-methyluracil, pseudoisocytosine, 5-methoxycytosine, 2-thiocytosine, 5-hydroxycytosine, $N^4$-methylcytosine, 5-hydroxymethylcytosine, hypoxanthine, $N^1$-methylguanine, $O^6$-methylguanine, $N^2$-methylguanine ($m^2G$), $N^2,N^2$-dimethylguanine ($m^{2,2}G$), $N^2,N^7$-dimethylguanine ($m^{2,7}G$), and isoguanine; wherein the seco (UNA) ribose moiety is a seco (UNA) ribose or a modified seco (UNA) ribose, and wherein one or both of the seco (UNA) ribose 2' or 3' carbons has a fluoro or a C1-C6 alkoxy substituent; and $N_2$ consists of (i) a base and (ii) a ribose moiety, wherein the base is selected from the group consisting of adenine, uridine, guanine, cytosine, $N^6$-methyladenine, $N^1$-methyladenine, pseudouruacil, $N^1$-methylpseudouracil, 5-iodouracil, 4-thiouracil, 2-thiouracil, 5-methyluracil, pseudoisocytosine, 5-methoxycytosine, 2-thiocytosine, 5-hydroxycytosine, $N^4$-methylcytosine, 5-hydroxymethylcytosine, hypoxanthine, $N^1$-methylguanine, $O^6$-methylguanine, $N^2$-methylguanine ($m^2G$), $N^2,N^2$-dimethylguanine ($m^{2,2}G$), $N^2,N^7$-dimethylguanine ($m^{2,7}G$), and isoguanine; wherein the $m^7G$ ribonucleotide is linked at its 5'-OH to the triphosphate bridge, wherein the triphosphate bridge is linked to a 5'-OH of the $N_1$ ribonucleotide, wherein $N_1$ nucleotide is linked via its 3'-OH to a phosphate, p, and wherein the phosphate is linked to a 5'-OH of the $N_2$ ribonucleotide; or a salt or solvated form thereof.

In some embodiments, the base of $N_1$ is adenine, uridine, guanine, or cytosine.

In some embodiments, the base of $N_1$ is adenine.

In some embodiments, the ribose moiety of $N_1$ consists of a modified seco (UNA) ribose and one or both of the ribose 2' or 3' carbons has a fluoro or a C1-C6 alkoxy substituent.

In some embodiments, the ribose moiety of $N_1$ consists of a modified seco (UNA) ribose and the 2' carbon has a fluoro or a C1-C6 alkoxy substituent.

In some embodiments, the ribose moiety of $N_1$ consists of a modified seco (UNA) ribose, wherein the ribose 2' carbon has a C1-C6 alkoxy substituent.

In some embodiments, the ribose moiety of $N_1$ consists of a modified seco (UNA) ribose, wherein the ribose 2' carbon has a methoxy substituent.

In some embodiments, the base of $N_2$ is selected from the group consisting of guanine, $N_1$-methylguanine, $O^6$-methylguanine, $m^2G$, $m^{2,2}G$, $m^{2,7}G$, and isoguanine.

In some embodiments, the base of $N_2$ is guanine, $N^1$-methylguanine, $O^6$-methylguanine, or isoguanine.

In some embodiments, the base of $N_2$ is guanine.

In some embodiments, the 2' carbon of at least one ribose of $m^7G$, $N_1$, or $N_2$ ribonucleotide is substituted by a C1-C6-alkoxy.

In some embodiments, at least one ribose of $N_1$ or $N_2$ ribonucleotide is substituted by a 2'-O-methyl.

In some embodiments, the triphosphate bridge consists of 1, 2, or 3 phosphorothioate groups.

In some embodiments, the compound is $m^7G(5')p_3$-seco-2'-OMeA-G, wherein seco-2'-OMeA is 2'-O-methyladenosine-seco(UNA)ribose and G is guanosine.

In another aspect, the compound increases the efficiency of $m^7G(5')p_3$-RNA produced by in vitro transcription compared to 3'-OMe-$m^7G(5')p_3G$.

In some embodiments, the in vitro transcription is mediated by T7 RNA polymerase or T6 RNA polymerase.

In another aspect, disclosed herein is a compound of formula $m^7G(5')p_3(5')N_1pN_2$, wherein the compound increases the yield of 5'-capped transcripts produced by in vitro transcription compared to ACRA, (e.g., transcription is mediated by T7 RNA polymerase or T6 RNA polymerase).

In another aspect, disclosed herein is a compound of formula $m^7G(5')ppp-N_1pN_2$, wherein $m^7G$ is a ribonucleotide consisting of $N^7$-methylguanine and a ribose, wherein ppp is a 5' to 5' triphosphate linkage; wherein $N_1$ comprises a seco (UNA) ribose optionally substituted at the 2' or 3' carbons with one or more fluoro or C1-C6 alkoxy substituents, and a base selected from the group consisting of adenine, uridine, guanine, cytosine, $N^6$-methyladenine, $N_1$-methyladenine, pseudouracil, $N^1$-methylpseudouracil, 5-iodouracil, 4-thiouracil, 2-thiouracil, 5-methyluracil, pseudoisocytosine, 5-methoxycytosine, 2-thiocytosine, 5-hydroxycytosine, $N^4$-methylcytosine, 5-hydroxymethylcytosine, hypoxanthine, $N^1$-methylguanine, $O^6$-methylguanine, $N^2$-methylguanine ($m^2G$), $N^2,N^2$-dimethylguanine ($m^{2,2}G$), $N^2,N^7$-dimethylguanine ($m^{2,7}G$), and isoguanine; wherein the seco (UNA) ribose moiety is a seco (UNA) ribose or a modified seco (UNA) ribose, and wherein one or both of the seco (UNA) ribose 2' or 3' carbons has a fluoro or a C1-C6 alkoxy substituent; and $N_2$ consists of (i) a base and (ii) a ribose moiety, wherein the base is selected from the group consisting of adenine, uridine, guanine, cytosine, $N^6$-methyladenine, $N^1$-methyladenine, pseudouruacil, $N^1$-methylpseudouracil, 5-iodouracil, 4-thiouracil, 2-thiouracil, 5-methyluracil, pseudoisocytosine, 5-methoxycytosine, 2-thiocytosine, 5-hydroxycytosine, $N^4$-methylcytosine, 5-hydroxymethylcytosine, hypoxanthine, $N^1$-methylguanine, $O^6$-methylguanine, $N^2$-methylguanine ($m^2G$), $N^2,N^2$-dimethylguanine ($m^{2,2}G$), $N^2,N^7$-dimethylguanine ($m^{2,7}G$), and isoguanine; and wherein the $m^7G$ ribonucleotide is linked at its 5'-OH to the triphosphate bridge, wherein the triphosphate bridge is linked to a 5'-OH of the $N_1$ ribonucleotide, wherein $N_1$ nucleotide is linked via its 3'-OH to a phosphate, p, wherein the phosphate is linked to a 5'-OH of the $N_2$ ribonucleotide; or a salt or solvated form thereof.

In some embodiments, the $m^7G$ ribonucleotide of the trinucleotide cap analog is modified so that the base is substituted with hypoxanthine, $m^7G$, $m^6G$, or isoguanine. In another aspect, one or both of the 2'-OH or the 3'OH groups of the ribose group of the $m^7G$ ribonucleotide are substituted by fluoro or C1-C6 alkoxy group, or the ribose is substituted by bicyclic (LNA) or seco (UNA) ribose.

In another aspect, disclosed herein is a method of synthesizing mRNA in vitro from DNA by using the trinucleotide cap analog to initiate transcription. In some embodiments, the in vitro transcription uses a DNA-dependent RNA polymerase (e.g., commercially available bacteriophage T7 RNA polymerase, T3 RNA polymerase, or SP6 RNA polymerase).

In another aspect, disclosed herein is an mRNA produced by in vitro transcription using the trinucleotide cap analog. In some embodiments, disclosed herein is an mRNA produced the description herein that initiates translation of a protein. In some embodiments, disclosed herein is an mRNA produced by the methods herein that suppresses translation of a protein. In some embodiments, disclosed herein is a pharmaceutical composition comprising the mRNA described herein and pharmaceutical excipients. In some embodiments, the pharmaceutical composition comprises the mRNA encapsulated in a liposomal nanoparticle.

In another aspect, disclosed herein is a method of treating a disease, comprising administering the pharmaceutical composition described herein to a subject in need thereof.

In yet another aspect, disclosed herein is a kit comprising the trinucleotide cap analog described herein. In some embodiments, the kit comprises a T7 RNA polymerase, a T3 RNA polymerase, or a SP6 RNA polymerase.

DETAILED DESCRIPTION

Figure 1:
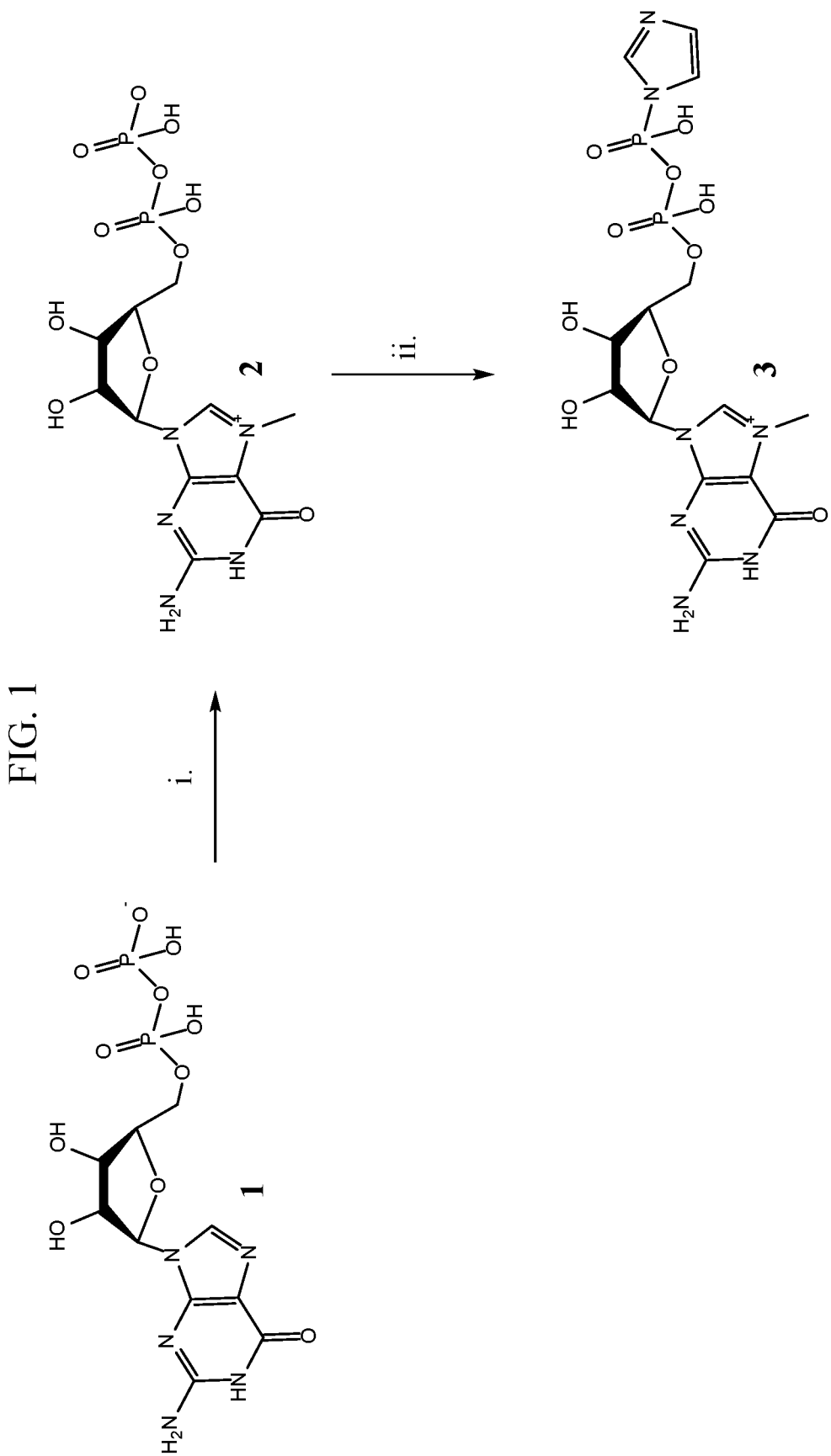
FIG. 1 shows synthesis of $m^7$GDP-IM (3) from GDP (1) by step i to intermediate $m^7$GDP (2) and further imidazole addition at step ii.

In order to increase the efficiency of in vitro transcription of m$^7$G(5')p$_3$-RNA, the present description provides a trinucleotide cap analog, m$^7$G(5')p$_3$(5')N$_1$pN$_2$.

In one aspect, disclosed herein is a compound of formula m$^7$G(5')p$_3$(5')N$_1$pN$_2$, wherein m$^7$G is a ribonucleotide consisting of N$^7$-methylguanine and a ribose or a modified ribose wherein one or both of the ribose 2' or 3' carbons has a fluoro or a C1-C6 alkoxy substituent; (5')p$_3$(5') is a 5' to 5' triphosphate linkage, wherein the triphosphate linkage may be substituted with one or more phosphorothioate groups; N$_1$ comprises a seco (UNA) ribose optionally substituted at the 2' or 3' carbons with one or more fluoro or C1-C6 alkoxy substituents, and a base selected from the group consisting of adenine, uridine, guanine, cytosine, N$^6$-methyladenine, N$^1$-methyladenine, pseudouracil, N$^1$-methylpseudouracil, 5-iodouracil, 4-thiouracil, 2-thiouracil, 5-methyluracil, pseudoisocytosine, 5-methoxycytosine, 2-thiocytosine, 5-hydroxycytosine, N$^4$-methylcytosine, 5-hydroxymethylcytosine, hypoxanthine, N$^1$-methylguanine, O$^6$-methylguanine, N$^2$-methylguanine (m$^2$G), N$^2$,N$^2$-dimethylguanine (m$^{2,2}$G), N$^2$,N$^7$-dimethylguanine (m$^{2,7}$G), and isoguanine; wherein the seco (UNA) ribose moiety is a seco (UNA) ribose or a modified seco (UNA) ribose, and wherein one or both of the seco (UNA) ribose 2' or 3' carbons has a fluoro or a C1-C6 alkoxy substituent; and N$_2$ consists of (i) a base and (ii) a ribose moiety, wherein the base is selected from the group consisting of adenine, uridine, guanine, cytosine, N$^6$-methyladenine, N$^1$-methyladenine, pseudouruacil, N$^1$-methylpseudouracil, 5-iodouracil, 4-thiouracil, 2-thiouracil, 5-methyluracil, pseudoisocytosine, 5-methoxycytosine, 2-thiocytosine, 5-hydroxycytosine, N$^4$-methylcytosine, 5-hydroxymethylcytosine, hypoxanthine, N$^1$-methylguanine, O$^6$-methylguanine, N$^2$-methylguanine (m$^2$G), N$^2$,N$^2$-dimethylguanine (m$^{2,2}$G), N$^2$,N$^7$-dimethylguanine (m$^{2,7}$G), and isoguanine; wherein the m$^7$G ribonucleotide is linked at its 5'-OH to the triphosphate bridge, wherein the triphosphate bridge is linked to a 5'-OH of the N$_1$ ribonucleotide wherein N$_1$ nucleotide is linked via its 3'-OH to a phosphate, p, wherein the base of N$_1$ is adenine, and wherein the phosphate is linked to a 5'-OH of the N$_2$ ribonucleotide; or a salt or solvated form thereof.

In another aspect disclosed herein is a compound of formula m$^7$G(5')p$_3$(5')N$_1$pN$_2$, wherein m$^7$G is a ribonucleotide consisting of N$^7$-methylguanine and a ribose; wherein (5')p$_3$(5') is a 5' to 5' triphosphate linkage, and wherein N$_1$ and N$_2$ are ribonucleotides, wherein one or both of N$^1$ and N$_2$ consist of a base selected from N$^6$-methyladenine, N$^1$-methyladenine, pseudouruacil, N$^1$-methylpseudouracil, 5-iodouracil, 4-thiouracil, 2-thiouracil, 5-methyluracil, pseudoisocytosine, 5-methoxycytosine, 2-thiocytosine, 5-hydroxycytosine, N$^4$-methylcytosine, 5-hydroxymethylcytosine, hypoxanthine, N$^1$-methylguanine, O$^6$-methylguanine, 1-methyl-guanosine, N$^2$-methyl-guanosine (m$^2$G), N$^2$,N$^2$-dimethyl-guanosine (m$^{2,2}$G), 2-methyl-2'-O-methyl-guanosine (m$^2$Gm), N$^2$,N$^2$-dimethyl-2'-O-methyl-guanosine (m$^{22}$Gm), 1-methyl-2'-O-methyl-guanosine, N$^2$,N$^7$-dimethyl-2'-O-methyl-guanosine (m$^{2,7}$Gm), or isoguanineadenine; and a ribose, a bicyclic (LNA) ribose, a seco (UNA) ribose, or a modified ribose wherein one or both of the ribose 2' or 3' carbons has a fluoro or a C1-C6 alkoxy substituent; and wherein the m$^7$G ribonucleotide is linked at its 5'-OH to the triphosphate bridge, wherein the triphosphate bridge is linked to a 5'-OH of the N$_1$ ribonucleotide, wherein N$_1$ nucleotide is linked via its 3'-OH to a phosphate, p, wherein the phosphate is linked to a 5'-OH of the N$_2$ ribonucleotide; or a salt or solvated form thereof.

One embodiment of m$^7$G(5')p$_3$(5')N$_1$pN$_2$ is wherein N$_1$ is a ribonucleotide consisting of adenine, uridine, guanine, or cytidine, preferably adenine.

Another embodiment of m$^7$G(5')p$_3$(5')N$_1$pN$_2$ is wherein N$_2$ consists of N$^1$-methylguanine, O$^6$-methylguanine, 1-methyl-guanosine, m$^2$G, m$^{2,2}$G, m$^2$Gm, m$^{2,2}$Gm, 1-methyl-2'-O-methyl-guanosine, m$^{2,7}$Gm, or isoguanineadenine.

Another embodiment of m$^7$G(5')p$_3$(5')N$_1$pN$_2$ is wherein N$_2$ consists of N$^1$-methylguanine, O$^6$-methylguanine, or isoguanineadenine.

Another embodiment of m$^7$G(5')p$_3$(5')N$_1$pN$_2$ is wherein N$_1$ consists of a LNA, a UNA, or a ribose wherein one or both of the ribose 2' or 3' carbons has a fluoro or a C1-C6 alkoxy substituent.

Another embodiment of m$^7$G(5')p$_3$(5')N$_1$pN$_2$ is wherein N$_2$ is a ribonucleotide consisting of adenine, uridine, guanine, or cytidine, preferably guanine.

Another embodiment of m$^7$G(5')p$_3$(5')N$_1$pN$_2$ is wherein N$_2$ is a ribonucleotide consisting of a LNA, a UNA, or a ribose wherein one or both of the ribose 2' or 3' carbons has a fluoro or a C1-C6 alkoxy substituent.

Another embodiment of m$^7$G(5')p$_3$(5')N$_1$pN$_2$ consists of m$^7$G(5')p$_3$AmpGm, wherein Am is 2'OMe-adenine and Gm is 2'OMe-guanine.

Another embodiment of m$^7$G(5')p$_3$(5')N$_1$pN$_2$ consists of m$^7$G(5')p$_3$m$^6$AmpGm, wherein $^6$mAm is 2'OMe-N$^6$methyladenine and Gm is 2'OMe-guanine.

Another embodiment of m$^7$G(5')p$_3$(5')N$_1$pN$_2$ consists of m$^7$G(5')p$_3$m$^6$AmpG$_{LNA}$, wherein $^6$mAm is 2'OMe-N$^6$methyladenine and G$_{LNA}$ is guanine bicyclic (LNA)-ribose. Another embodiment is wherein at least one ribose of the m$^7$G, N$_1$, or N$_2$ ribonucleotide is a LNA.

Another embodiment of m$^7$G(5')p$_3$(5')N$_1$pN$_2$ consists of m$^7$G(5')p$_3$m$^6$AmpG$_{UNA}$, wherein $^6$mAm is 2'OMe-N$^6$methyladenine and G$_U$NA is guanine seco(UNA)ribose. Another embodiment is wherein at least one ribose of m$^7$G, N$_1$, or N$_2$ ribonucleotide is a UNA.

Another embodiment of m$^7$G(5')p$_3$(5')N$_1$pN$_2$ is, wherein at least one ribose of m$^7$G, N$_1$, or N$_2$ ribonucleotide is substituted by a 2'-C1-C6-alkoxy, preferably 2'-OMe.

Another embodiment of m$^7$G(5')p$_3$(5')N$_1$pN$_2$ is wherein the triphosphate bridge consisting of 1, 2, or 3 phosphorothioate groups.

Another embodiment of m$^7$G(5')p$_3$(5')N$_1$pN$_2$ is wherein the compound increases the yield of 5'-capped transcripts produced by in vitro transcription compared to ACRA, for example, transcription is mediated by T7 RNA polymerase or T6 RNA polymerase.

Another aspect of the description is a compound of formula m$^7$G(5')ppp-N$_1$pN$_2$, wherein m$^7$G is a ribonucleotide consisting of N$^7$-methylguanine and a ribose, wherein ppp is a 5' to 5' triphosphate linkage; wherein N$_1$ and N$_2$ are ribonucleotides, wherein one or both of N$_1$ and N$_2$ ribonucleotides consist of a base selected from adenine, uracil, cytosine, or guanine; and a bicyclic (LNA) ribose, a seco (UNA) ribose, or a modified ribose wherein one or both of the ribose 2' or 3' carbons has a fluoro or a C1-C6 alkoxy substituent; and wherein the m$^7$G ribonucleotide is linked at its 5'-OH to the triphosphate bridge, wherein the triphosphate bridge is linked to a 5'-OH of the N$_1$ ribonucleotide wherein N$_1$ nucleotide is linked via its 3'-OH to a phosphate, p, wherein the phosphate is linked to a 5'-OH of the N$_2$ ribonucleotide; or a salt or solvated form thereof.

In one aspect of the description, the m$^7$G ribonucleotide of the trinucleotide cap analog is modified so that the base is substituted with hypoxanthine, m$^1$G, m$^6$G, or isoguanine. In another aspect, one or both of the 2'-OH or the 3'OH groups of the ribose group of the m$^7$G ribonucleotide are substituted by fluoro or C1-C6 alkoxy group, or the ribose is substituted by bicyclic (LNA) or seco (UNA) ribose. In either case, the N$_1$ and N$_2$ ribonucleotides each consists of a base independently selected from adenine, uracil, cytosine, guanine, or an analog thereof, and a sugar selected from ribose, modified ribose, bicyclic ribose, or seco ribose.

Another aspect of the description is a method of synthesizing mRNA in vitro from DNA by using the trinucleotide cap analog according to description herein to initiate transcription. In preferred embodiments, the in vitro transcription uses a DNA-dependent RNA polymerase (e.g., commercially available bacteriophage T7 RNA polymerase, T3 RNA polymerase, or SP6 RNA polymerase).

Another aspect of the description is mRNA produced by in vitro transcription using the trinucleotide cap analog described herein. A preferred embodiment is an mRNA produced the description herein that initiates translation of a protein. Another preferred embodiment is an mRNA produced by the methods herein that suppresses translation of a protein. Another embodiment is a pharmaceutical composition comprising the mRNA described herein and pharmaceutical excipients. In a preferred embodiment, the pharmaceutical composition comprises the mRNA encapsulated in a liposomal nanoparticle.

Another aspect of the description is a method of treating a disease, comprising administering the pharmaceutical composition described herein to a subject in need thereof.

Another aspect of the description is a kit comprising the trinucleotide cap analog described herein. In a preferred embodiment, the kit comprises a T7 RNA polymerase, a T3 RNA polymerase, or a SP6 RNA polymerase.

Definitions that follow will apply to the description herein. Whenever appropriate, terms used in the singular will also include the plural and vice versa. In the event that any definition set forth below conflicts with the usage of that word in any other document, including any document incorporated herein by reference, the definition set forth below shall always control for purposes of interpreting this specification and its associated claims unless a contrary meaning is clearly intended (for example in interpreting the document where the term is originally used). The use of "or" herein means "and/or" unless stated otherwise or where the use of "and/or" is clearly inappropriate. The use of "a" herein means "one or more" unless stated otherwise or where the use of "one or more" is clearly inappropriate. The use of "comprise," "comprises," "comprising," "include," "includes," and "including" are interchangeable and not intended to be limiting.

As used herein, "Me" means "CH$_3$", and "OCH$_3$" or "OMe" denotes an oxygen atom bound to a methyl group, "CHO" denotes a carbon atom, C, bonded to a hydrogen atom, H, and double-bonded to an oxygen atom, O, (O=CH—) and "Et" denotes "C$_2$H$_5$".

"Cap" herein means a non-extendible trinucleotide that facilitates translation and/or localization, and/or prevents degradation of an RNA transcript when incorporated at the 5' end of an RNA transcript. It consists in nature of the modified base 7-methylguanosine joined in the opposite orientation, 5' to 5' rather than 5' to 3', to the rest of the RNA molecule via three phosphate groups i.e., PI-guanosine-5'-yl P3-7-methylguanosine-5'-yl triphosphate (m$^7$G5'ppp5'G).

"Hydrate" is a solvate wherein the solvent molecule is H$_2$O.

A "cap analog" means a structural derivative of an RNA cap that may differ by as little as a single element. Cap analog is used for the synthesis of 5' capped RNA molecules in in vitro transcription reactions. Substitution of cap analog for a portion of the GTP in a transcription reaction results in the incorporation of the cap structure into a corresponding fraction of the transcripts. Capped mRNAs are generally translated more efficiently in reticulocyte lysate and wheat germ in vitro translation systems. In vitro transcripts must be capped for microinjection experiments because uncapped mRNAs are rapidly degraded. Cap analogs can also be used as a highly specific inhibitor of the initiation step of protein synthesis.

"Enzymatically incorporatable" means a nucleotide is capable of being enzymatically incorporated onto the terminus, e.g. 3' terminus, of a polynucleotide chain, or internally through nick-translation of a polynucleotide chain, through action of a template-dependent or template-independent polymerase enzyme. A nucleotide-5'-triphosphate is an example of an enzymatically incorporatable nucleotide.

"Enzymatically extendable" or "3' extendable" means a nucleotide or polynucleotide that is capable of being appended to a nucleotide or polynucleotide by enzyme action. A polynucleotide containing a 3' hydroxyl group is an example of an enzymatically extendable polynucleotide.

A "locked nucleic acid" (LNA) means a ribonucleotide in which there is a bridge between the 2'O and 4'C methylene bicyclonucleotide monomers.

A "nucleobase" means a nitrogen containing heterocyclic moiety nucleobase. Non-limiting examples of suitable nucleobases include: adenine, cytosine, guanine, thymine, uracil, or analogs thereof, e.g., 5-propynyl-uracil, 2-thio-5-propynyl-uracil, 5-methylcytosine, pseudoisocytosine, 2-thiouracil, 2-thiothymine, 2-aminopurine, N9-(2-amino-6-chloropurine), N9-(2,6-diaminopurine), hypoxanthine, N9-(7-deaza-guanine), N9-(7-deaza-8-aza-guanine) and N8-(8-aza-7-deazaadenine).

A "ribonucleotide" or "nucleotide" herein means a compound consisting of a nucleobase linked to the C-1' carbon of a ribose sugar or analog thereof. The ribose or analog may be substituted or unsubstituted. Substituted ribose sugars include, but are not limited to, those riboses in which one or more of the carbon atoms, preferably the 3'-carbon atom, is substituted with one or more of the same or different substituents such as —R, —OR, —NRR or halogen (e.g., fluoro, chloro, bromo, or iodo), where each R group is independently —H, $C_1$-$C_6$ alkyl or $C_6$-$C_{14}$ aryl or arylalkyl. Typically, when the nucleobase is A or G, the ribose sugar is attached to the N$^9$-position of the nucleobase. When the nucleobase is C, T or U, the pentose sugar is attached to the N$^1$-position of the nucleobase. Examples of ribose analogs include arabinose, 2'-O-methyl ribose, UNA, and LNA analogs.

A "ribonucleotide" means a phosphate ester of a ribonucleotide as a monomer unit or within a polynucleotide.

A "nucleotide triphosphate" means a nucleotide with a triphosphate ester group at the 5' position.

"Alkyl", "C1, C2, C3, C4, C5 or C6 alkyl" or "C1-C6 alkyl" is intended to include C1, C2, C3, C4, C5 or C6 straight chain (linear) saturated aliphatic hydrocarbon groups and C3, C4, C5 or e branched saturated aliphatic hydrocarbon groups. For example, C1-C6 alkyl is intended to include C1, C2, C3, C4, C5 and C6 alkyl groups. Examples of alkyl include, moieties having from one to six carbon atoms, such as, but not limited to, methyl, ethyl, n-propyl, i-propyl, n-butyl, s-butyl, t-butyl, n-pentyl, s-pentyl or n-hexyl.

In certain embodiments, a straight chain or branched alkyl has six or fewer carbon atoms (e.g., C1-C6 for straight chain, C3-C6 for branched chain), and in another embodiment, a straight chain or branched alkyl has four or fewer carbon atoms. Ribonucleotides and/or ribonucleotides comprise ribose or a ribose analog.

"Ribose analog" includes, e.g., substituted or unsubstituted furanoses having more or fewer than 5 ring atoms, e.g., erythroses and hexoses and substituted or unsubstituted 3-6 carbon acyclic sugars (e.g., UNA). Typical substituted furanoses and acyclic sugars are those in which one or more of the carbon atoms are substituted with one or more of the same or different —R, —OR, —NRR or halogen groups, where each R is independently —H, ($C_1$-$C_6$) alkyl or ($C_1$-$C_{14}$) aryl. Examples of substituted furanoses having 5 ring atoms include but are not limited to 2'-deoxyribose, 2'-($C_1$-$C_6$)alkylribose, 2'-($C_1$-$C_6$)alkoxyribose, 2'-($C_5$-$C_{14}$)aryloxyribose, 2',3'-dideoxyribose, 2',3'-didehydroribose, 2'-deoxy-3'-haloribose, 2'-deoxy-3'-fluororibose, 2'-deoxy-3'-chlororibose, 2'-deoxy-3'-aminoribose, 2'-deoxy-3'-($C_1$-$C_6$)alkylribose, 2'-deoxy-3'-($C_1$-$C_6$)alkoxyribose, 2'-deoxy-3'-($C_5$-$C_{14}$)aryloxyribose, 3'-($C_1$-$C_6$)alkylribose-5'-triphosphate, 2'-deoxy-3'-($C_1$-$C_6$)alkylribose-5'-triphosphate, 2'-deoxy-3'-($C_1$-$C_6$)alkoxyribose-5'-triphosphate, 2'-deoxy-3'-($C_5$-$C_{14}$)atyloxyribose-5'-triphosphate, 2'-deoxy-3'-haloribose-5'-triphosphate, 2'-deoxy-3'-aminoribose-5'-triphosphate, 2',3'-dideoxyribose-5'-triphosphate or 2',3'-didehydroribose-5'-triphosphate. Further sugar analogs also include so called locked nucleic acids (LNAs) having the structure

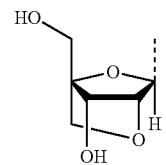

and those described in WO 99/14226 and Koskin, 2001, *J Org Chem*, 66:8504-12 (incorporated herein by reference) and unlocked ribonucleic acid (UNA) having the structure

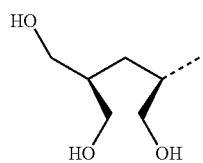

and those described in U.S. Pat. Nos. 9,297,009 and 9,051,570 (incorporated herein by reference).

"Polynucleotide", "oligonucleotide" and "nucleic acid" mean single stranded or double stranded polymers of nucleotide monomers, including ribonucleotides (RNA) and 2'-deoxyribonucleotides (DNA) linked by internucleotide phosphodiester bond linkages. A polynucleotide may be composed entirely of deoxyribonucleotides, entirely of ribonucleotides or chimeric mixtures thereof.

"Substituted" means substitution with specified groups other than hydrogen, or with one or more groups, moieties or radicals which can be the same or different, with each, for example, being independently selected.

The trinucleotide compounds of described herein form salts that are also within the scope of this disclosure. Reference to a trinucleotide compound herein is understood to include reference to salts thereof, unless otherwise indicated.

"Salt(s)" mean acidic salts formed with inorganic and/or organic acids, as well as basic salts formed with inorganic and/or organic bases. In addition, when a trinucleotide compound contains both a basic moiety, such as, but not limited to a pyridine or imidazole, and an acidic moiety, such as, but not limited to a carboxylic acid, zwitterions ("inner salts") may be formed and are included within the term "salt(s)" as used herein. The salts can be pharmaceutically acceptable (i.e., non-toxic, physiologically acceptable) salts, although other salts are also useful. Salts of the trinucleotide compounds may be formed, for example, by reacting the trinucleotide compounds with an amount of acid or base, such as an equivalent amount, in a medium such as one in which the salt precipitates or in an aqueous medium followed by lyophilization.

Exemplary acid addition salts include acetates, adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, benzenesulfonates, toluenesulfonates, nitrobenzene sulfonates, 2-napthalenesulfonates, nicotinates, nitrates, oxalates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates) undecanoates, and the like. Additionally, acids which are generally considered suitable for the formation of pharmaceutically useful salts from basic pharmaceutical compounds. These disclosures are incorporated herein by reference herein.

Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, trialkyl amines such as triethyl amine, and salts with amino acids such as arginine, lysine and the like. Basic nitrogen-containing groups may be quarternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl, and stearyl chlorides, bromides and iodides), arylalkyl halides (e.g., benzyl and phenethyl bromides), allylic and propargylic halides such as 1-bromo-2-propene and 1-bromo-2-propyne, and others.

All such acid and base salts are intended to be pharmaceutically acceptable salts within the scope of the disclosure and all acid and base salts are considered equivalent to the free forms of the corresponding compounds for purposes of the disclosure.

"Solvate" means a physical association of a trinucleotide compound of this disclosure with one or more solvent molecules. This physical association involves varying degrees of ionic and covalent bonding, including hydrogen bonding. In certain instances, the solvate will be capable of isolation, for example when one or more solvent molecules are incorporated in the crystal lattice of the crystalline solid. Solvate encompasses both solution-phase and isolatable solvates. Non-limiting examples of suitable solvates include water, ethanolates, methanolates, and the like. Trinucleotide compounds of the disclosure can exist in unsolvated and solvated forms, including hydrated forms. In general, the solvated forms, with pharmaceutically acceptable solvents such as water, ethanol and the like, are equivalent to the unsolvated forms for the purposes of this disclosure.

Trinucleotide compounds of the disclosure, and solvates thereof, may exist in their tautomeric form. All such tautomeric forms are contemplated herein as part of the present disclosure.

All stereoisomers (for example, geometric isomers, optical isomers and the like) of the present trinucleotide compounds (including those of the salts, solvates and prodrugs of the trinucleotide compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this disclosure. Individual stereoisomers of the trinucleotide compounds of this disclosure may, for example, be substantially free of other isomers, or may be admixed, for example, as racemates or with all other, or other selected, stereoisomers. The chiral centers of the trinucleotide compounds herein can have the S or R configuration as defined by the IUPAC 1974 Recommendations. The use of the terms "salt", "solvate", and the like, is intended to equally apply to the salt, solvate and prodrug of enantiomers, stereoisomers, rotamers, tautomers, or racemates of the disclosed trinucleotide compounds.

The trinucleotide compounds of the disclosure may also contain unnatural proportions of atomic isotopes at one or more of the atoms that constitute such trinucleotide compounds. Unnatural proportions of an isotope may be defined as ranging from the amount found in nature to an amount consisting of 100% of the atom in question. For example, the trinucleotide compounds may incorporate radioactive isotopes, such as, for example, tritium ($^3H$), iodine-125 ($^{125}I$) or carbon-14 ($^{14}C$), or non-radioactive isotopes, such as deuterium ($^2H$), carbon-13 ($^{13}C$), or isotopes of nitrogen, oxygen and sulfur. Such isotopic variations can provide additional utilities to those described elsewhere within this application. For instance, isotopic variants of the trinucleotide compounds of the invention may find additional utility, including but not limited to, as diagnostic and/or imaging reagents, or as cytotoxic/radiotoxic therapeutic agents. Additionally, isotopic variants of the trinucleotide compounds of the invention can have altered pharmacokinetic and pharmacodynamic characteristics which can contribute to enhanced safety, tolerability or efficacy during treatment. All isotopic variations of the trinucleotide compounds of the description herein, whether radioactive or not, are intended to be encompassed within the scope of the description herein.

"Inhibitors" and "antagonists", or "activators" and "agonists" mean inhibitory or activating molecules, respectively, for example, for the activation of, e.g., a ligand, receptor, cofactor, gene, cell, tissue, or organ. Inhibitors are molecules that decrease, block, prevent, delay activation, inactivate, desensitize, or down-regulate, e.g., a gene, protein, ligand, receptor, or cell. Activators are molecules that increase, activate, facilitate, enhance activation, sensitize, or up-regulate, e.g., a gene, protein, ligand, receptor, or cell. An inhibitor may also be defined as a molecule that reduces, blocks, or inactivates a constitutive activity. An "agonist" is a molecule that interacts with a target to cause or promote an increase in the activation of the target. An "antagonist" is a molecule that opposes the action(s) of an agonist. An antagonist prevents, reduces, inhibits, or neutralizes the activity of an agonist, and an antagonist can also prevent, inhibit, or reduce constitutive activity of a target, e.g., a target receptor, even where there is no identified agonist.

The "activity" of a molecule may describe or refer to the binding of the molecule to a ligand or to a receptor; to catalytic activity; to the ability to stimulate gene expression or cell signaling, differentiation, or maturation; to antigenic activity; to the modulation of activities of other molecules; and the like.

"Proliferative activity" means an activity that promotes, that is necessary for, or that is specifically associated with, for example, normal cell division, as well as cancer, tumors, dysplasia, cell transformation, metastasis, and angiogenesis.

mRNA Synthesis

The trinucleotide cap analogs disclosed herein are used for improving the synthesis of 5' capped RNA molecules in in vitro transcription reactions. Substitution of cap analog for a portion of the GTP in a transcription reaction results in the incorporation of the cap structure into a corresponding fraction of the transcripts.

Transcription of RNA usually starts with a nucleotide triphosphate (usually a purine, A or G). When transcription occurs in vitro, it typically includes a phage RNA polymerase such as T7, T3 or SP6, a DNA template containing a phage polymerase promoter, nucleotides (ATP, GTP, CTP and UTP) and a buffer containing magnesium salt. The synthesis of capped RNA includes the incorporation of a cap (e.g., $m^7GpppG$) or a cap analog (such as those described herein) in the transcription reaction. Excess cap to GTP (e.g., 4:1) increases the opportunity that each transcript will have a 5' cap. The mMESSAGE mMACHINE® SP6 Transcription Kit and SP7 Ultra Kit (ThermoFisher Scientific) recommends this ratio and will typically yield 80% capped RNA to 20% uncapped RNA, although total yields of total RNA are lower as GTP concentration becomes rate limiting as GTP is necessary for the elongation of the transcript.

Capped mRNAs are generally translated more efficiently in reticulocyte lysine and wheat germ in vitro translation systems. It is important that in vitro transcripts be capped for microinjection experiments because uncapped mRNAs are rapidly degraded. Cap analogs are also used as a highly specific inhibitor of the initiation step of protein synthesis.

The 5' cap structure enhances the translation of mRNA by helping to bind the eukaryotic ribosome and assuring recognition of the proper AUG initiator codon. This function may vary with the translation system and with the specific mRNA being synthesized. The consensus sequence 5'-GC-CACCAUGG-3', also known as the "Kozak" sequence, is considered to be the strongest ribosomal binding signal in eukaryotic mRNA. For efficient translation initiation, the key elements are the 5' G residue at the +1 position and the A residue at the 3' position of the mRNA.

The mRNA can be transfected into a cell to be translated intracellularly. Methods of transfection are known to those of skill in the art and include microinjection, electroporation, chemical treatments and the like. Cells for use in in vivo translation include any patient cell for which it is desired to express a protein of interest. Cells include hematopoietic cells (e.g., T cells, dendritic cells, macrophages, etc.), bone marrow cells, tissue culture cells, germ cells, and the like.

Compositions comprising modified capped RNA as described herein can be used for in vitro transcription, in vitro translation, and in vivo translation, for example. Current biotechnology efforts for in vitro, in situ, and in vivo protein production will also benefit from these methods and compositions. Further, compositions provided herein are useful for therapeutic purposes. For example, the present technology may be useful for generating vaccines against infectious diseases or cancers. Alkyne-derivatized capped RNA can be used to produce non-infectious particles of Venezuelan Equine Encephalitis virus containing an RNA encoding immunogen. These non-replicating viral particles can be injected into humans where they can enter host cells. Once in the host cell, the viral particles dissociate and the mRNA encoding the immunogen is translated into protein. These proteins can induce an immune response. These types of vaccines are expected to be useful for human immunodeficiency virus (HIV), feline immunodeficiency virus, human papilloma virus type 16, tumors, lassa virus, Ebola virus, Marburg virus, anthrax toxin from Bacillus anthraces, and botulinum toxin. These vaccine strategies can require large quantities of capped RNA. The present methods facilitate such synthesis and subsequent purification of capped RNA so as to make these vaccines commercially feasible. As well, strategies to increase the percentage of full length capped RNA in a transcription reaction leading to a more homogenous product will be preferred in the vaccine industry as highly pure components are usually required for human use. In addition, researchers prefer to use products that are as pure as possible to minimize the number of variables in an experiment. As well, the purer the product, the more potent it is.

Such oligomers or oligonucleotides may be prepared by solid state synthesis or by other means known to those skilled in the art. For example, 2'-O-alkyl guanosine phosphoramidites and derivatives thereof may be incorporated into oligonucleotides using standard phosphoramidite chemistry. Incorporation of 2'-O-alkyl guanosine nucleotides may confer desirable characteristics to an oligonucleotide such as enhanced resistance to nuclease.

"Oligonucleotide" or "oligomer" as used herein means a polynucleotide formed from naturally occurring bases and furanosyl groups joined by native phosphodiester bonds. Oligonucleotides of the description herein will, of course, comprise at least one 2'-O-alkyl guanosine or derivative thereof. Thus, this term effectively refers to naturally occurring species or synthetic species formed from naturally occurring subunits or their close homologs. The term "oligonucleotide" or "oligomer" may also refer to moieties which have portions similar to naturally occurring oligonucleotides, but which have non-naturally occurring portions. Thus, oligonucleotides may have altered sugars, altered base moieties, or altered inter-sugar linkages. Exemplary among these are the phosphorothioate and other sulfur-containing species which are known for use in the art. In accordance with some preferred embodiments, at least some of the phosphodiester bonds of the oligonucleotide have been substituted with a structure which functions to enhance the stability of the oligonucleotide or the ability of the oligonucleotide to penetrate into the region of cells where the messenger RNA is located. It is preferred that such substitutions comprise phosphorothioate bonds, phosphotri-esters, methyl phosphonate bonds, short chain alkyl or cycloalkyl structures or short chain heteroatomic or heterocyclic structures. Other preferred substitutions are $CH_2$—

NH—O—CH$_2$, CH$_2$—N(CH$_3$)—O—CH$_2$, CH$_2$—O—N(CH$_3$)—CH$_2$, CH$_2$—N(CH$_3$)—N(CH$_3$)—CH$_2$ and O—N(CH$_3$)—CH$_2$—CH$_2$ structures where phosphodiester intersugar linkage is replaced by the substitutions. Also preferred are morpholino structures. In accordance with other preferred embodiments, the phosphodiester bonds are substituted with other structures which are, at once, substantially non-ionic and non-chiral, or with structures which are chiral and enantiomerically specific. Persons of ordinary skill in the art will be able to select other linkages for use in practice of the invention.

Oligonucleotides may also include species which include at least some modified base forms. Thus, purines and pyrimidines other than those normally found in nature may be so employed. Suitable bases include modifications on the furanosyl portion of the nucleotide subunits, in addition to 2'-O-alkyl modifications of the description herein, may also be effected as long as the essential tenets of this invention are adhered to. Examples of such modifications are 2'-halogen-substituted nucleotides. Some specific examples of modifications at the 2' position of sugar moieties which are useful in the description herein are OH, SH, SCH$_3$, F, OCN, O(CH$_2$)$_n$NH$_2$, Cl, Br, CN, CF$_3$, OCF$_3$, S—, OC1-OC12, O-alkenyl, O-alkynal, or N-alkyl; S- or N-alkenyl; SOCH$_3$, SO$_2$CH$_3$; ONO$_2$; NO$_2$; N$_3$; NH$_2$; heterocycloalkyl; heterocycloalkaryl; aminoalkylamino; polyalkylamino; substituted silyl; an RNA cleaving group; a conjugate; a reporter group; an intercalator; a group for improving the pharmacokinetic properties of an oligonucleotide; or a group for improving the pharmacodynamic properties of an oligonucleotide and other substituents having similar properties. Sugar mimetics such as cyclobutyls may also be used in place of the pentofuranosyl group. Oligonucleotides may also comprise other modifications consistent with the spirit of this invention. Such oligonucleotides are best described as being functionally interchangeable with yet structurally distinct from natural oligonucleotides. All such oligonucleotides are comprehended by this invention so long as they effectively function as subunits in the oligonucleotide.

Preferably oligonucleotides of the description herein are from about 6 to about 50 nucleotides in length. In still more preferred embodiments of the description herein oligonucleotides are from about 12 to about 20 nucleotides in length.

Intercalators are molecules which insert themselves between neighboring bases of an oligonucleotide, e.g., acridine.

Reporter molecules are molecules which may aid in the identification of a molecule, either visually or otherwise. For example, biotin and various fluorophores are effective reporter groups.

Conjugates, or bifunctional linkers effectively join two groups. Some conjugates are commercially available such as biotin or 3' maleimidobenzoyl-N-hydroxy-succinimide.

Pharmacodynamic property improvement means, in this context, improved oligonucleotide uptake, enhanced oligonucleotide resistance to degradation, and/or strengthened sequence-specific hybridization with RNA. Such groups do not initiate chemical reactions. Groups that enhance the pharmacodynamic properties of an oligonucleotide preferably include alkyl chains, polyamines, ethylene glycols, polyamides, alkyl chains, aminoalkyl chains and amphipathic moieties. Pharmacokinetic property improvement means improved oligonucleotide uptake, distribution, metabolism or excretion.

Antisense therapy involves the use of oligonucleotides which are specifically hybridizable to target RNA or DNA. Oligonucleotides of the description herein are preferably specifically hydridizable with a target region. "Specifically hybridizable" means capable of forming a stable duplex with a target DNA or RNA. Upon binding to, or forming a stable duplex with, the target RNA or DNA, the antisense oligonucleotide can selectively inhibit the genetic expression of these nucleic acids or can induce some other events such as destruction of a targeted RNA or DNA or activation of gene expression. Destruction of targeted RNA can be effected by RNase H activation or by linking strand cleavers to the oligonucleotide.

In some embodiments of the description herein the oligonucleotide portions of trinucleotide compounds of the description herein are at least 30%, 40%, 50%, 60%, 70%, 80%, 90% or 100% complementary to a target sequence. In preferred embodiments of the description herein the oligonucleotide portions of trinucleotide compounds of the description herein are at least 60%, 70%, or 80% complementary to a target sequence. 100% complementarity of the oligonucleotide portions of trinucleotide compounds of the description herein to a target sequence is most preferred. In preferred embodiments of the description herein, the oligonucleotide portions may be specifically hybridizable with DNA or RNA from *Candida*, papilloma virus, Epstein Barr virus, rhinovirus, hepatitis, human immunodeficiency virus, herpes simplex virus, influenza virus and cytomegalovirus.

2-O-alkyl guanosine containing oligonucleotides of the description herein may be used to modulate the production of protein by contacting a selected sequence of RNA or DNA coding for a selected protein with an 2'-O-alkyl guanosine containing oligonucleotide of the description herein having a sequence of nucleotide bases specifically hybridizable with said selected sequence of RNA or DNA coding for said protein.

The oligonucleotides of the description herein can be used in diagnostics, therapeutics and as research reagents. For therapeutic use, an animal having a disease characterized by the undesired production of a protein is contacted with an oligonucleotide of the description herein having a sequence of nucleotide bases specifically hybridizable with a selected sequence of RNA or DNA coding for said protein.

Pharmaceutical Use

Another use of compositions described herein involves isolating dendritic cells (DCs) from a patient and then transfecting the dendritic cells with derivatized capped RNA as described herein encoding immunogen. The dendritic cells translate the derivatized capped RNA into at least one protein that induces an immune response against this protein.

Morse, 2002, *Int J Gastrointest Cancer,* 32:1-6, discloses that immunotherapy with dendritic cells loaded with CEA capped RNA is safe and feasible for pancreatic cancer patients. Heiser, 2002, *J Clin Invest,* 109:409-17, discloses that introducing at least one single capped RNA species into immature dendritic cells induced a specific T-cell response. The cap analogs provided herein can be used for providing mRNAs for antigen delivery to DCs for the purpose of immunotherapy against cancer and infectious diseases.

Other uses include reprogramming differentiated cells to pluripotency and/or to re-program pluripotent cells using capped RNA described herein to specifically differentiate cell types by continuous transfection of specific derivatized-capped mRNAs over a time-period necessary for changing the cell differentiation.

Trinucleotide compounds of the disclosure may be in the form of compositions suitable for administration to a subject. In general, such compositions are "pharmaceutical compositions" comprising at least one trinucleotide compound and one or more pharmaceutically acceptable or physiologically acceptable diluents, carriers or excipients. In certain embodiments, trinucleotide compounds of the disclosure are present in a therapeutically acceptable amount. The pharmaceutical compositions may be used in the methods of the description herein; thus, for example, the pharmaceutical compositions can be administered ex vivo or in vivo to a subject in order to practice the therapeutic and prophylactic methods and uses described herein.

The pharmaceutical compositions of the description herein can be formulated to be compatible with the intended method or route of administration; exemplary routes of administration are set forth herein. Furthermore, the pharmaceutical compositions may be used in combination with other therapeutically active agents or trinucleotide compounds as described herein in order to treat or prevent the diseases, disorders and conditions as contemplated by the description herein.

The description herein contemplates the administration of trinucleotide compounds of the disclosure, and compositions thereof, in any appropriate manner. Suitable routes of administration include oral, parenteral (e.g., intramuscular, intravenous, subcutaneous (e.g., injection or implant), intraperitoneal, intracisternal, intraarticular, intraperitoneal, intracerebral (intraparenchymal) and intracerebroventricular), nasal, vaginal, sublingual, intraocular, rectal, topical (e.g., transdermal), sublingual and inhalation.

Trinucleotide compounds of the disclosure may be administered to a subject in an amount that is dependent upon, for example, the goal of administration (e.g., the degree of resolution desired); the age, weight, sex, and health and physical condition of the subject to which the formulation is being administered; the route of administration; and the nature of the disease, disorder, condition or symptom thereof. The dosing regimen may also take into consideration the existence, nature, and extent of any adverse effects associated with the agent(s) being administered. Effective dosage amounts and dosage regimens can readily be determined from, for example, safety and dose-escalation trials, in vivo studies (e.g., animal models), and other methods known to the skilled artisan.

In general, dosing parameters dictate that the dosage amount be less than an amount that could be irreversibly toxic to the subject (the maximum tolerated dose (MTD)) and not less than an amount required to produce a measurable effect on the subject. Such amounts are determined by, for example, the pharmacokinetic and pharmacodynamic parameters associated with ADME, taking into consideration the route of administration and other factors.

An effective dose (ED) is the dose or amount of an agent that produces a therapeutic response or desired effect in some fraction of the subjects taking it. The "median effective dose" or ED50 of an agent is the dose or amount of an agent that produces a therapeutic response or desired effect in 50% of the population to which it is administered. Although the ED50 is commonly used as a measure of reasonable expectance of an agent's effect, it is not necessarily the dose that a clinician might deem appropriate taking into consideration all relevant factors. Thus, in some situations the effective amount is more than the calculated ED50, in other situations the effective amount is less than the calculated ED50, and in still other situations the effective amount is the same as the calculated ED50.

The amount and frequency of administration of the trinucleotide compounds of this disclosure and/or the pharmaceutically acceptable salts thereof will be regulated according to the judgment of the attending clinician considering such factors as age, condition and size of the patient as well as severity of the symptoms being treated.

EXAMPLES

Aspects of the present teachings may be further understood in light of the following examples, which should not be construed as limiting the scope of the present teachings in any way.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

Example 1

2-amino-9-((2S,3R,4S,5S)-3,4-dihydroxy-5-(((hydroxy ((hydroxy(1H-imidazol-1-yl)phosphoryl)oxy)phosphoryl) oxy)methyl)tetrahydrofuran-2-yl)-7-methyl-6-oxo-6,9-dihydro-1H-purin-7-ium ($m^7$GDP-IM, FIG. 1, compound 3). Synthesis of $m^7$GDP-IM from GDP is done by a two-step process according to Piecyk, 2012, *Tetrahedron Letters*, 53:4843-47 (hereby incorporated by reference), First, GDP (compound 1) is reacted with methyl iodide in DMSO to produce $m^7$GDP (compound 2, step i). One equivalent of $m^7$GDP is combined with 20 equivalents of imidazole, 2 equivalents of 2,2'-dithiophyridine, and triethylamine in anhydrous dimethylformamide (DMF) and stirred for 6-8 hours at room temperature (step ii). The imidazole product is precipitated from a solution of anhydrous sodium perchlorate in dry acetone and, after cooling to 4° C., the precipitate is filtered, washed in acetone, and dried overnight under vacuum to yield $m^7$GDP-IM (compound 3).

Example 2

Figure 2:
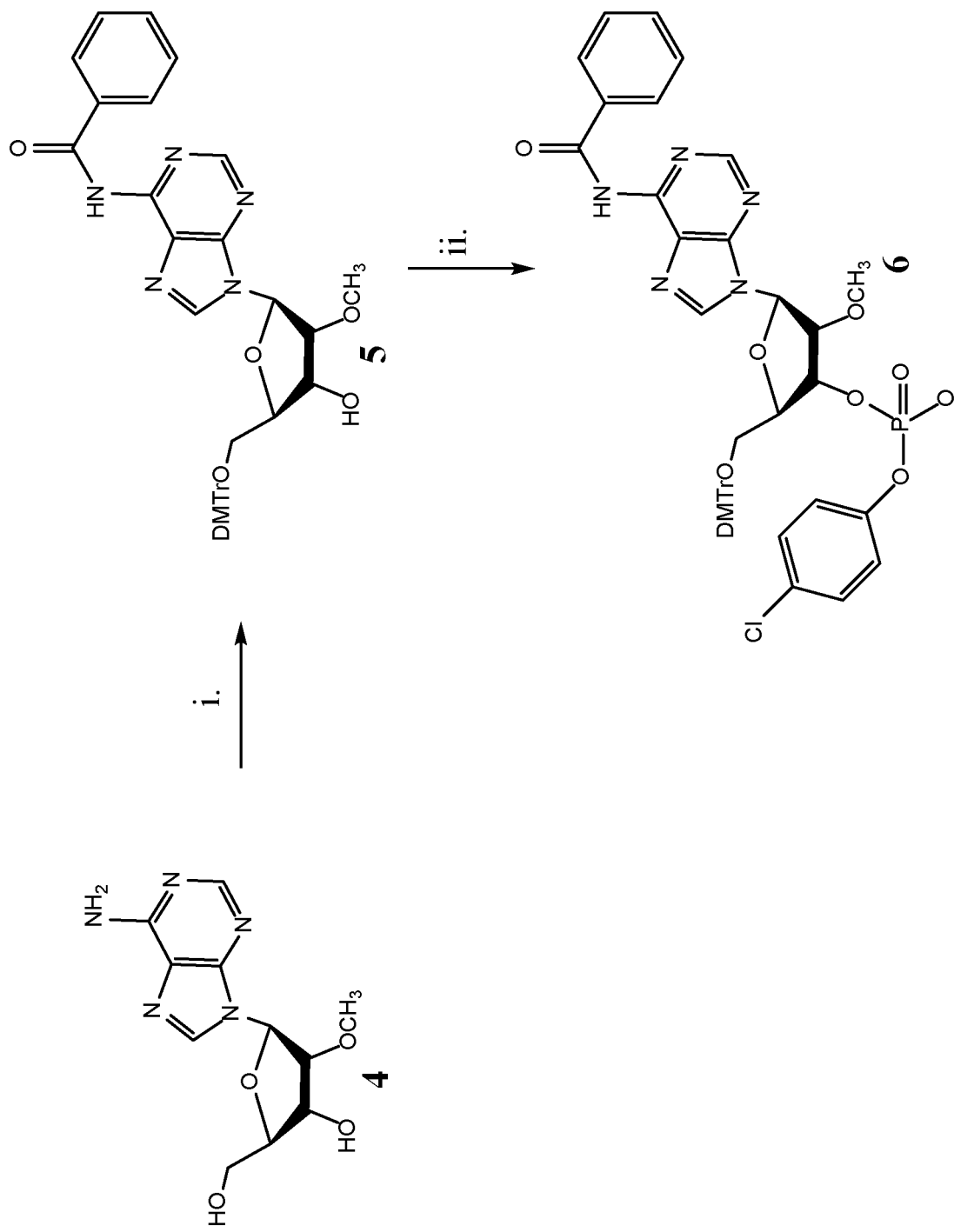
FIG. 2 shows synthesis of 5'-O-DMT-2'O-Me-$N^6$benzoyl-AMP-PhC (6) from 2'OMe-adenosine (4) to first form a TMS-modified, benzoyl-$m^6$-2'-OMe-adenosine which is benzoylated, then desilylated, and further protected as a DMTr ether (5) at step i. The introduction of the phosphate moiety (step ii) then gives 6.

(2R,3S,4S,5R)-5-(6-benzamido-9H-purin-9-yl)-2-(hydroxy-DMT)-4-methoxytetrahydrofuran-3-yl (4-chlorophenyl) phosphate (5'-O-DMT-2'O-Me-$N^6$benzoyl-AMP-PhCl, FIG. 2, compound 6) is prepared in two steps. First, commercially available 2'OMe-adenosine (compound 4) is reacted with benzoyl chloride in pyridine to acylate $N^6$ by the method of Zhu, 2003, *Synthetic Communications*, 33:1233-43 (hereby incorporated by reference). 2'OMe-adenosine is reacted with 1.1 equivalents of TMSCl per OH group together with 1.2 equivalents of benzoyl chloride to produce TMS-modified, benzoyl-$m^6$-2'-OMe-adenosine. The TMSA groups are removed under aqueous acidic conditions in THF-TFA. Further, the 5'-hydroxy of benzoyl-$m^6$-2'-OMe-adenosine is reacted with DMT to form an ether (step ii) (compound 5) according to the method of WO 99/14266 (hereby incorporated by reference) by preparing a anhydrous pyridine solution of the nucleotide, adding an excess of 4,4'-dimethoxytrityl chloride, stirring at room temperature for 2 hours, quenching the reaction with ice cold water, and extracting the product with DCM. The combined organic phases are washed with $NaHCO_3$-saturated water, brine, and dried $Na_2SO_4$. Phosphorylated adenosine is produced from DMT protected compound 5 by the method of Lewdorowicz, 2007, *Nucleotides, Nucleotides, and Nucleic Acids*, 26:1339-48 (hereby incorporated by reference) by reaction with 4-chlorophenyl dichlorophosphate as a 3'-O-phosphorylating agent (step ii) to produce 5'O-DMT-2'-O-Me-$N^6$benzoyl-AMP-PhCl (compound 6).

Example 3

Figure 3:
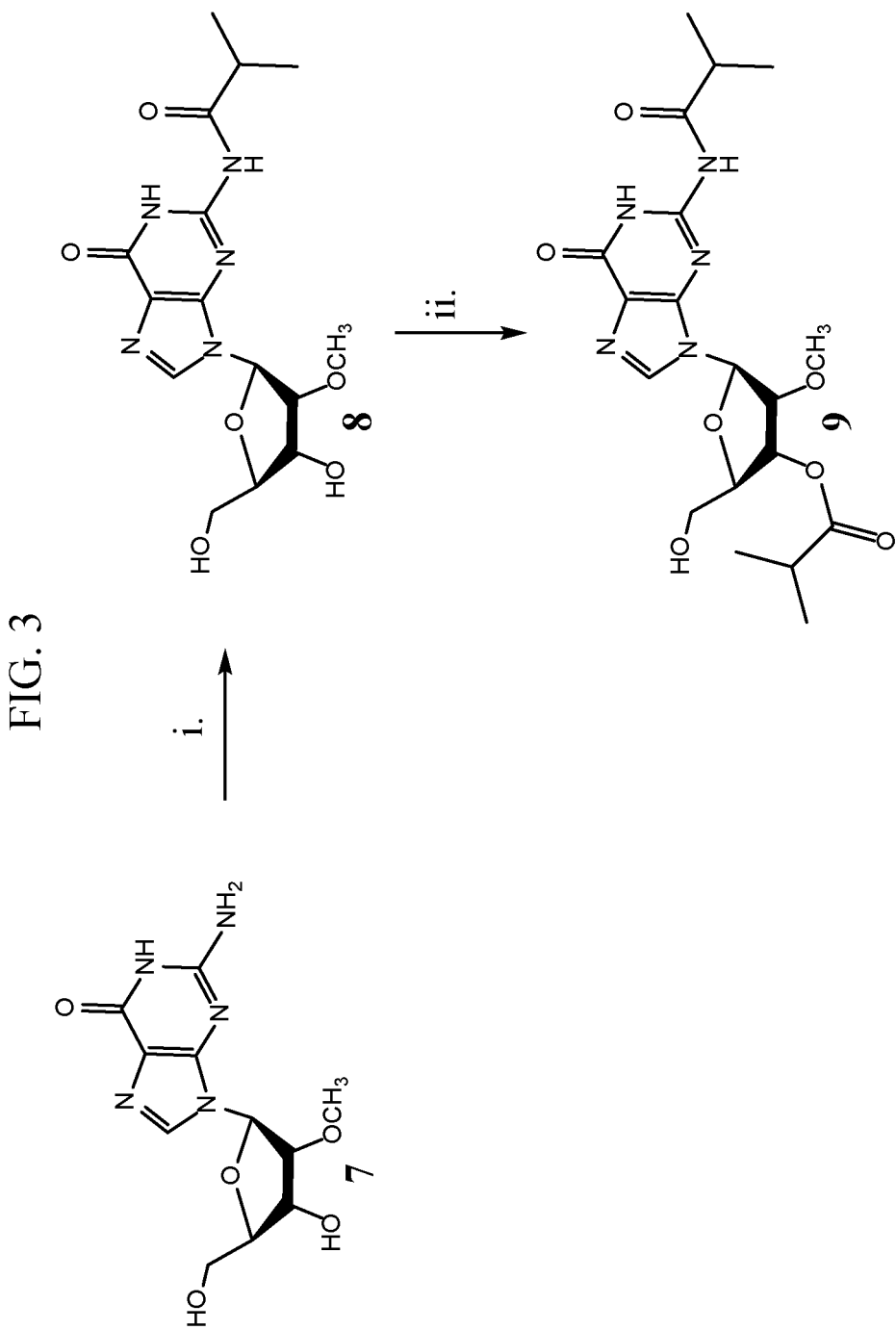
FIG. 3 shows synthesis of 2'-O-Me, 3'-O-isobutyryl, $N^2$-isobutyrylguanosine (9) from 2'OMe-guanosine (7) to produce intermediate $N^2$-isobuyryl-2'-O-methylguanosine (8) in step i, in which the 5'-OH is protected as a DMTr ether, then the 3'-OH is isobutyrylated and finally the DMTr group is removed in step ii to give 9.

(2R,3S,4S,5R)-2-(hydroxymethyl)-4-methoxy-5-(6-oxo-2-propionamido-1,6-dihydro-9H-purin-9-yl)tetrahydrofuran-3-yl isobutyrate (2'-O-Me,3'-O-isobutyryl,$N^2$-isobutyrylguanosine; FIG. 3, compound 9). Compound 9 is synthesized by the method of U.S. Pat. No. 7,101,993 (hereby incorporated by reference) from commercially available 2'OMe-guanosine (FIG. 7, step i). 2'-O-methylguanosine (compound 7) in pyridine is cooled in an ice bath and 6 equivalents of trimethylsilyl chloride (TMSCl) is added and mixed for 30 minutes, and isobutyryl chloride is added and stirred for 4 hours. Water is added and the mixture is stirred for 30 minutes and concentrated $NH_4OH$ is added and the solution is evaporated in vacuo to produce the $N^2$-isobuyryl-2'-O-methylguanosine compound 8. The 5'-hydroxy group is protected with a DMT group, the 3'-hydroxy group is subject to isobutyrylation, and the DMT group is removed by treatment with 5% trichloroaceteic acid to produce protected 2'OMe guanine compound 9 (step ii).

Example 4

Figure 4:
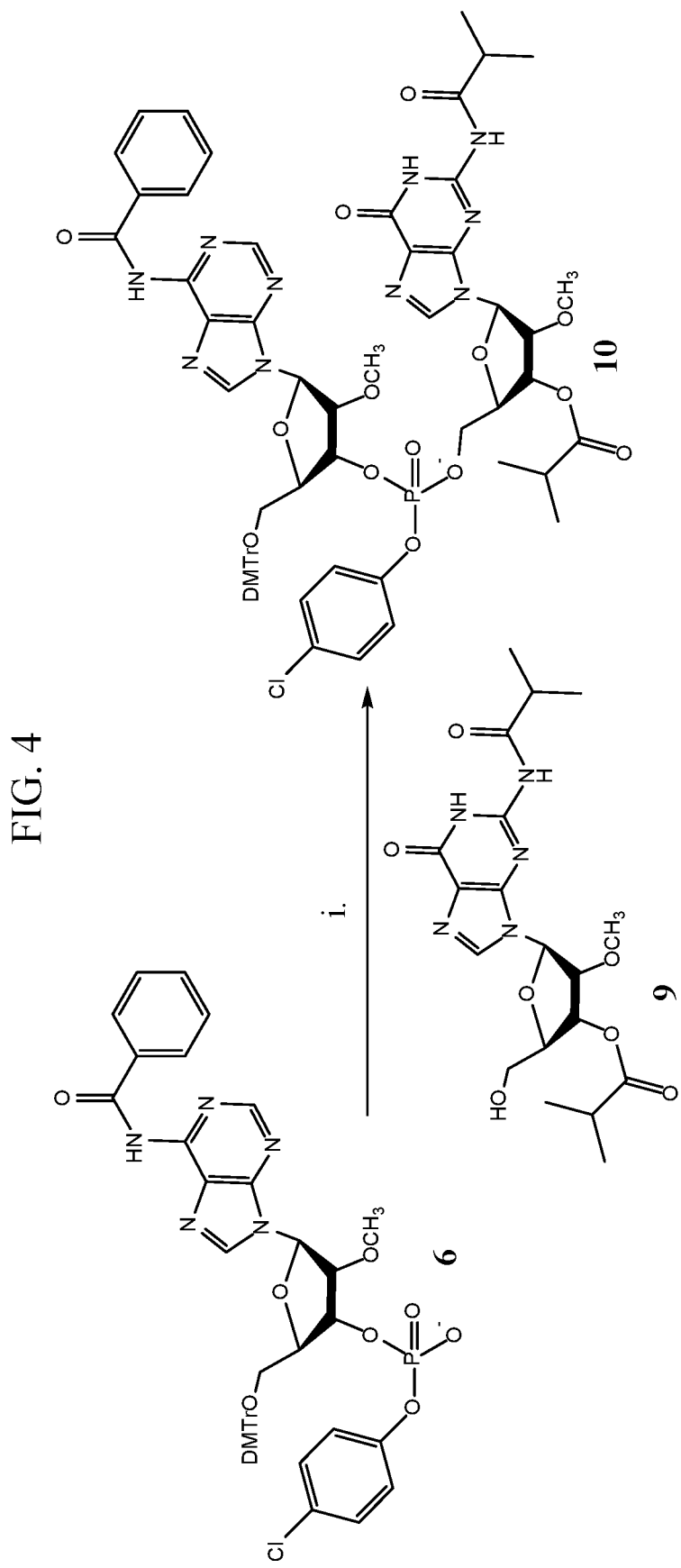
FIG. 4 shows synthesis of protected 2'-OMeAp-2'-OMeG dinucleotide (10) in step i by reaction of 3'-p-2'-OMeA (6) with 2'OMe guanosine (9).
Figure 5:
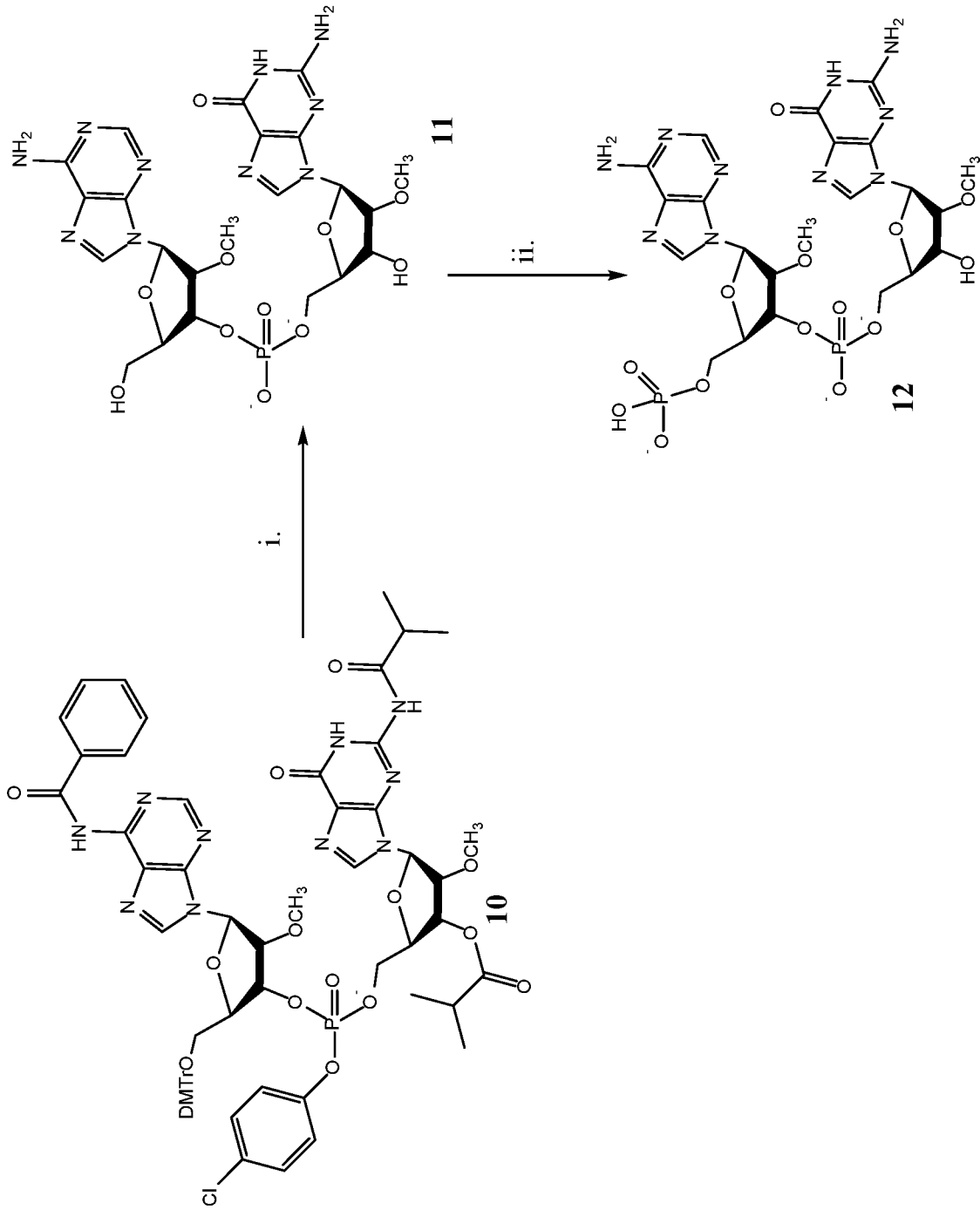
FIG. 5 shows removal of the protective groups of 2'OMeAp2'OMeG dinucleotide (10) in two steps: (i) to produce a 2'-OMeA-2'-OMeG dinucleotide compound 11 and phosphate introduction (ii) to produce 2'OMeAp2'OMeG dinucleotide 5'-monophosphate (12).

((2R,3S,4S,5R)-3-(((((2R,3S,4S,5R)-5-(2-amino-6-oxo-1,6-dihydro-9H-purin-9-yl)-3-hydroxy-4-methoxytetrahydrofuran-2-yl)methoxy)oxidophosphoryl)oxy)-5-(6-amino-9H-purin-9-yl)-4-methoxytetrahydrofuran-2-yl)methyl hydrogen phosphate (p-2'OMeAp-2'-OMeG, FIG. 5, compound 12). Protected 2'OMeAp2'OMeG dinucleotide, compound 10 (FIG. 4), was produced by combining 3'-p-2'-OMeA compound 6 (Example 2) with protected 2'-OMe guanosine compound 9 (Example 3) by the method of Lewdorowicz 2007. First, 3'-p-2'-OMeA compound 6 was mixed with an equivalent of 2'OMe guanosine compound 9 in anhydrous acetonitrile and the mixture was dried by evaporation. A solution of 2,4,6,-triisopropylbenzenesulfonyl chloride and N-methylimidazole in acetonitrile was added and the mixture was reacted for 4 hours to produce the protected 2'-OMeAp-2'-OMeG dinucleotide compound 10 (FIG. 4, step i).

The protective groups of 2'OMeAp2'OMeG dinucleotide compound 10 were removed (FIG. 5, step i) using known reactions, e.g., by a method selected from Lewdorowicz 2007; Huss, 1988, *J Org Chem*, 53:499-506; Zhou, 1986, *Tetrahedron*, 42:4149-56; Reese, 1986, *Tetrahedron Letters*, 27:2291-94; Abramova, 2008, *Biorg Med Chem*, 16:9127-32; Abramova, 2013, *Beilstein J Org Chem*, 9:2898-909; Hashmi, 1994, *Nucleotides & Nucleotides*, 13:1059-67; Hsu, 1985, *Nucleotides & Nucleotides*, 4:377-89; Puech, 1988, *J Med Chem*, 31:1897-907 (hereby incorporated by reference) (FIG. 5, step i) were removed to produce a 2'-OMeA-2'-OMeG dinucleotide compound 11. The 5'-hydroxy group of the adenosine group was phosphorylated according to the method of Lewdorowicz 2007 (FIG. 5, step ii). Phosphorus trichloride oxide in trimethyl phosphate was cooled to 4° C. and the 5'-O-guanine-adenine dinucleotide-3'-O compound 10 was added and stirred at 4° C. for 3 hours. Tetraethylammoniuum bromide (TEAB) was added to neutralize the mixture to produce the 2'OMeAp2'OMeG dinucleotide 5'-monophosphate (FIG. 5, compound 12).

Example 5

Figure 6:
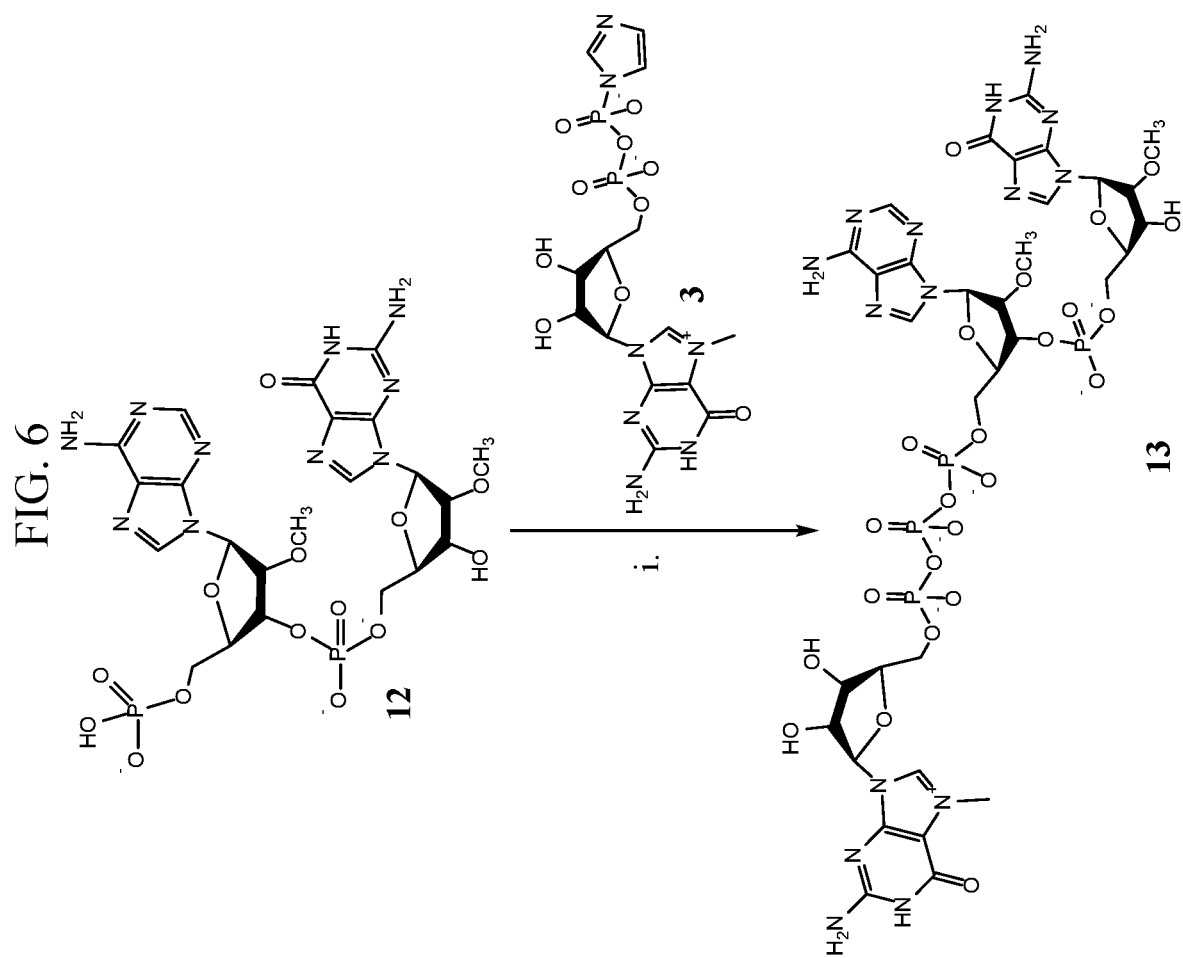
FIG. 6 shows synthesis of $m^7G(5')$ppp2'OMeAp2'OMeG (13) by reaction (i) of the ammonium salt of pApG (12) with the sodium salt of $m^7$GDP-IM (3).

Trinucleotide cap analog, $m^7G(5')ppp2'OMeAp2'OMeG$ (FIG. 6, compound 13). The trinucleotide cap analog is produced by the method of Lewdorowicz 2007. A mixture of ammonium salt of pApG (compound 12 produced in Example 4), four equivalents of a sodium salt of $m^7$GDP-IM (compound 1 produced in Example 1), and $ZnCl_2$ in DMF is stirred for 2 days at room temperature. The reaction is quenched by addition of water to yield $m^7G(5')$ppp2'OMeAp2'OMeG (compound 13).

Example 6

Figure 7:
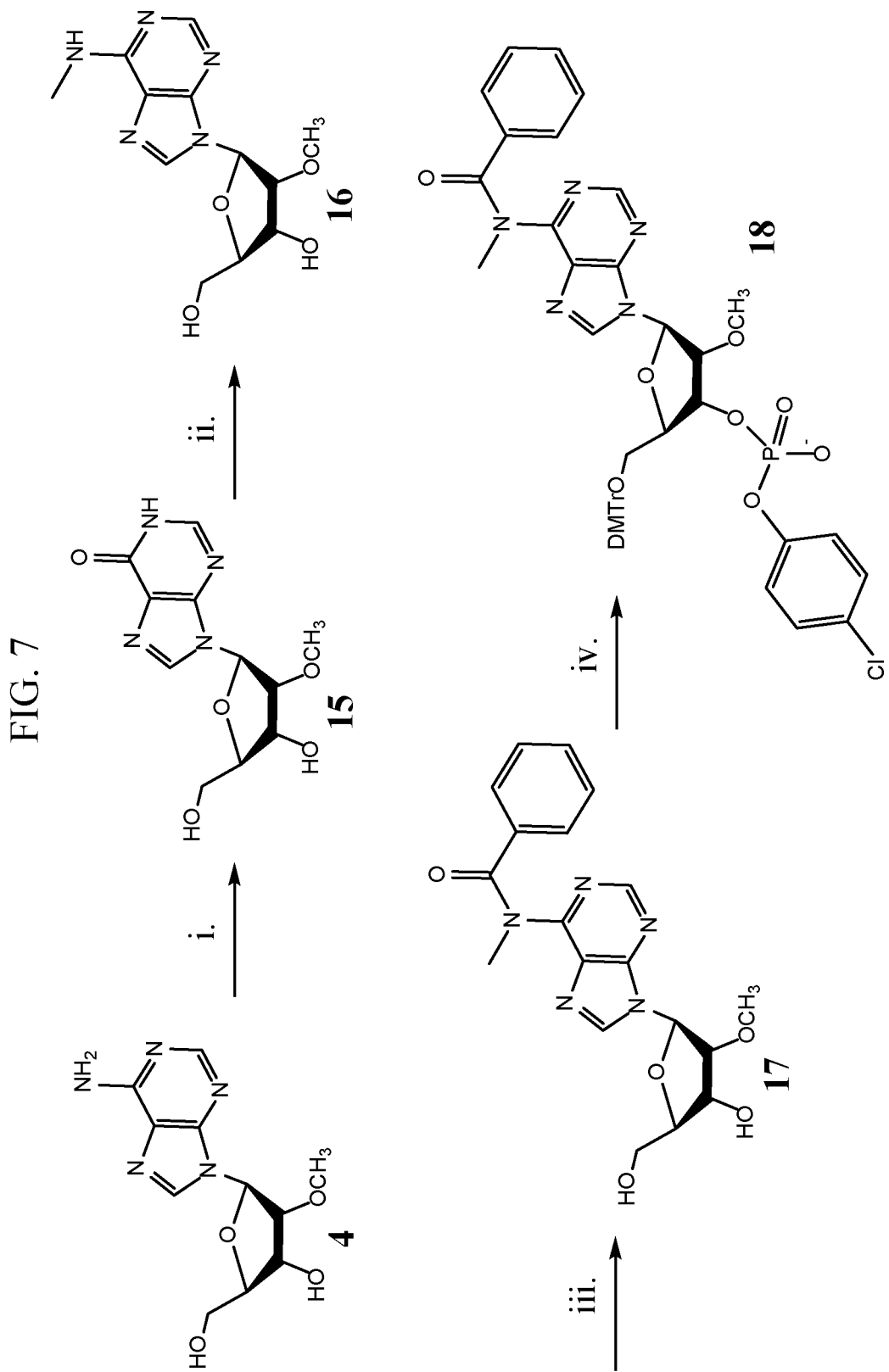
FIG. 7 shows synthesis of $m^6$-benzoyl-2'-OMe-AMP-PhCl (18) from 2'OMe-adenosine (4) by first producing intermediate 15 (i), converting to intermediate 16 (ii), forming TMS-modified, mono-benzoylated $m^6$2'OMe-adenosine which is desilylated to give (17) (iii), and protection of the 5'-OH as a DMTr ether followed by phosphate introduction (iv) gives 18.

4-chlorophenyl ((2R,3S,4S,5R)-2-(O-DMT)-4-methoxy-5-(6-(N-methylbenzamido)-9H-purin-9-yl)tetrahydrofuran-3-yl) phosphate ($m^6$-benzoyl-2'-OMe-AMP-PhCl, FIG. 7 compound 18). Commercially available 2'OMe-adenosine compound 4 was diazotized in aqueous acetic acid with nitrous acid to give compound 15 (step i) by the method of Hyde, 2003, *J Med Chem*, 46:1878-85 (hereby incorporated by reference). Compound 15 was converted to a compound 16 by the method of Miller, 2015, *J Med Chem*, 58:6248-6263 (hereby incorporated by reference) (step ii). The $m^62'$OMe-adenosine product (compound 16) was protected by the method of Zhu, 2003, *Synthetic Communications*, 33:1233-43 (hereby incorporated by reference) (step iii). The adenosine compound was reacted with 1.1 equivalents of TMSCl per hydroxy group together with 1.2 equivalents of benzoyl chloride to produce TMS-modified, mono-benzoylated $m^62'$OMe-adenosine. The TMSA groups were removed under aqueous acidic conditions in THF-TFA to give compound 17 (step iii). The 5'-hydroxy was reacted with DMT-Cl to form an ether and the phosphorylated adenosine compound 18 was produced as in Example 2 by reaction with 4-chlorophenyl dichlorophosphate as a 3'-O-phosphorylating agent (FIG. 7, step iv) to produce benzoyl-3'-p-$m^62'$-OMeA (compound 18).

Example 7

Figure 8:
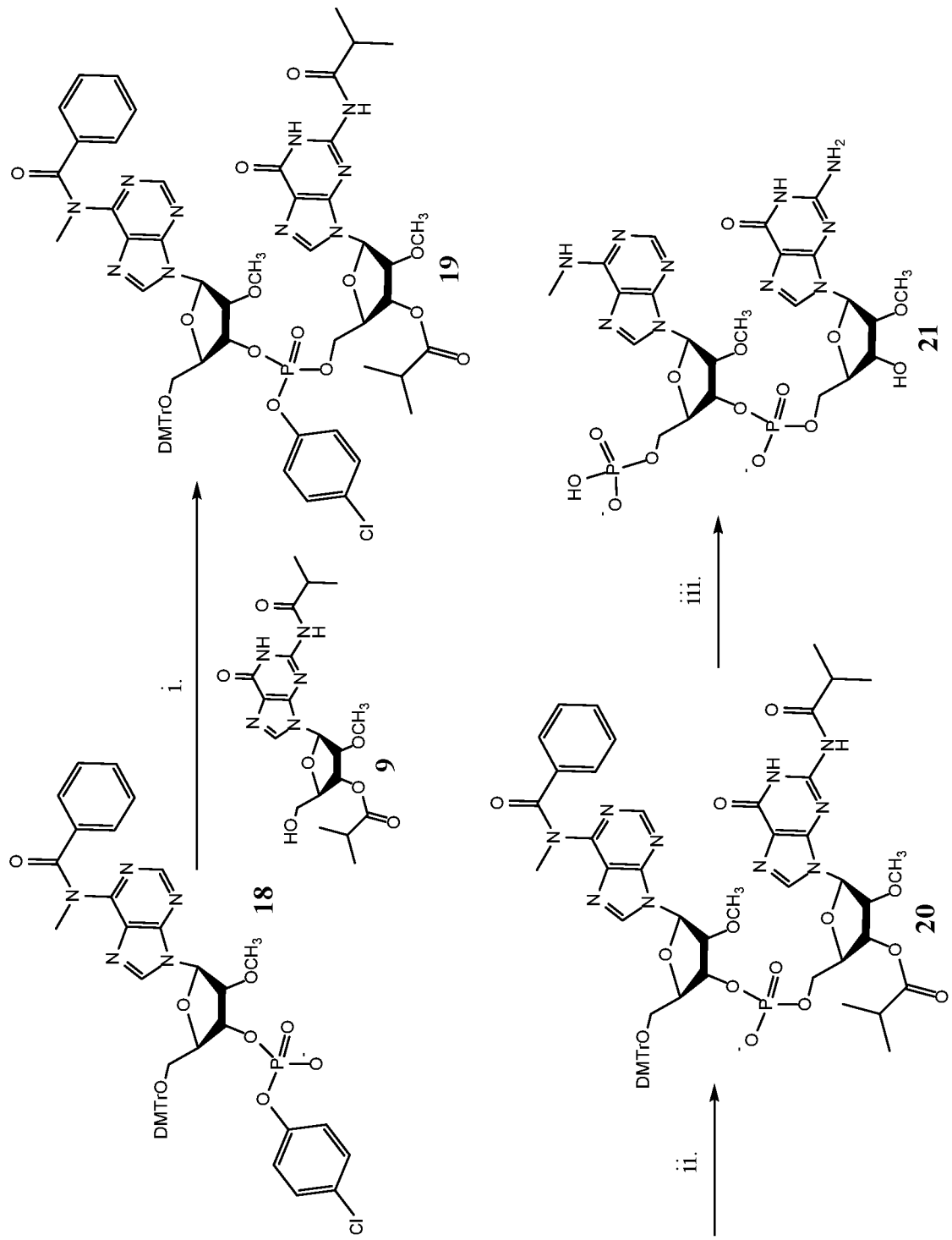
FIG. 8 shows formation of dinucleotide m$^6$2'OMeAp2'OMeG (21) by combining benzoyl-3'-p-m$^6$2'-OMeA (18) with protected 2'OMe adenosine (9) to produce intermediate m$^6$2'OMeAp2'OMeG dinucleotide (19) in step i. The protective groups of m$^6$2'OMeAp2'OMeG dinucleotide intermediate compound are removed (ii) to produce m$^6$2'OMeA-2'OMeG dinucleotide (20), which is phosphorylated (iii) to give 21.

Dinucleotide $m^62'$OMeAp2'OMeG (compound 21, FIG. 8). Compound 21 is produced by combining benzoyl-3'-p-$m^62'$-OMeA compound 18 (Example 7) with protected 2'OMe adenosine compound 9 (Example 3) by the method of Lewdorowicz 2007. First, 3'-p-2'-OMeA compound 18 is mixed with 1 equivalent of 2'OMe guanosine compound 9 in anhydrous acetonitrile and the mixture is dried by evaporation. A solution of 2,4,6,-triisopropylbenzenesulfonyl chloride and N-methylimidazole in acetonitrile is added and reacted for 4 hours to produce the protected $m^62'$OMeAp2'OMeG dinucleotide compound 19 (FIG. 8, step i).

The protective groups of $m^62'$OMeAp2'OMeG dinucleotide intermediate compound are removed (FIG. 8, step ii) as described in Example 4 to produce $m^62'$OMeA-2'OMeG dinucleotide compound 20. The 5'-hydroxy group of the adenosine group is phosphorylated according to the method of Lewdorowicz 2007 (FIG. 8, step iii). Phosphorus trichloride oxide in trimethyl phosphate is cooled to 4° C. and $m^62'$-OMeA-2'-OMeG is added and stirred at 4° C. for 3 hours. Tetraethylammoniuum bromide (TEAB) is added to neutralize the mixture to produce the $m^62'$OMeAp2'OMeG dinucleotide 5'-monophosphate (FIG. 8, compound 21).

Example 8

Figure 9:
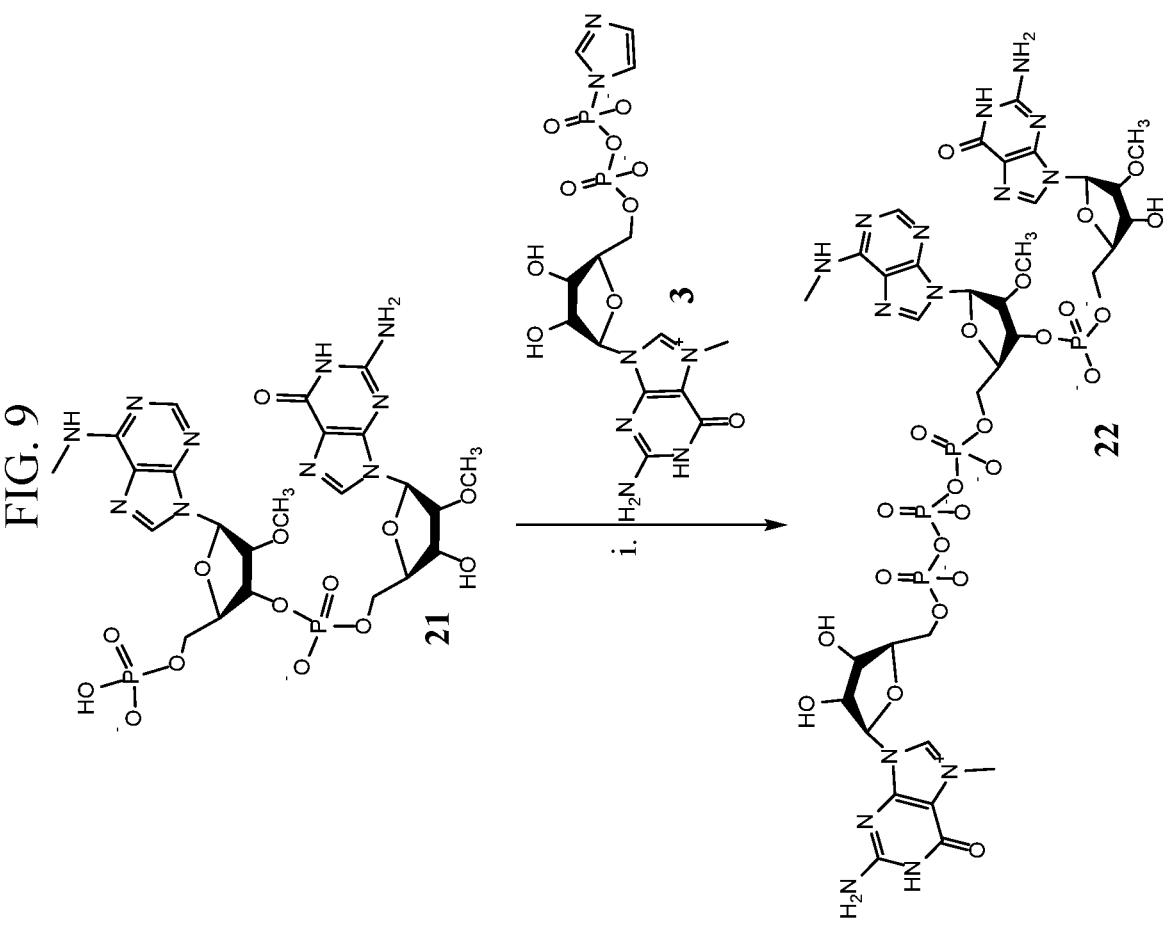
FIG. 9 shows production of trinucleotide cap analog, m$^7$G(5')ppp m$^6$2'OMeAp2'OMeG (22) from the ammonium salt of pApG (21) and the sodium salt of m$^7$GDP-IM (3).

Trinucleotide Cap Analog, $m^7G(5')$ppp $m^62'$OMeAp2'OMeG (compound 22, FIG. 9). The trinucleotide cap analog is produced by the method described in Example 5. A mixture of ammonium salt of pApG (compound 21 produced in Example 7), four equivalents of a sodium salt of $m^7$GDP-IM (compound 3 produced in Example 1), and ZnCl$_2$ in DMF is stirred for 2 days at room temperature. The reaction is quenched by addition of water to yield m$^7$G(5')pppm$^6$2'OMeAp2'OMeG (compound 22).

Example 9

Figure 10:
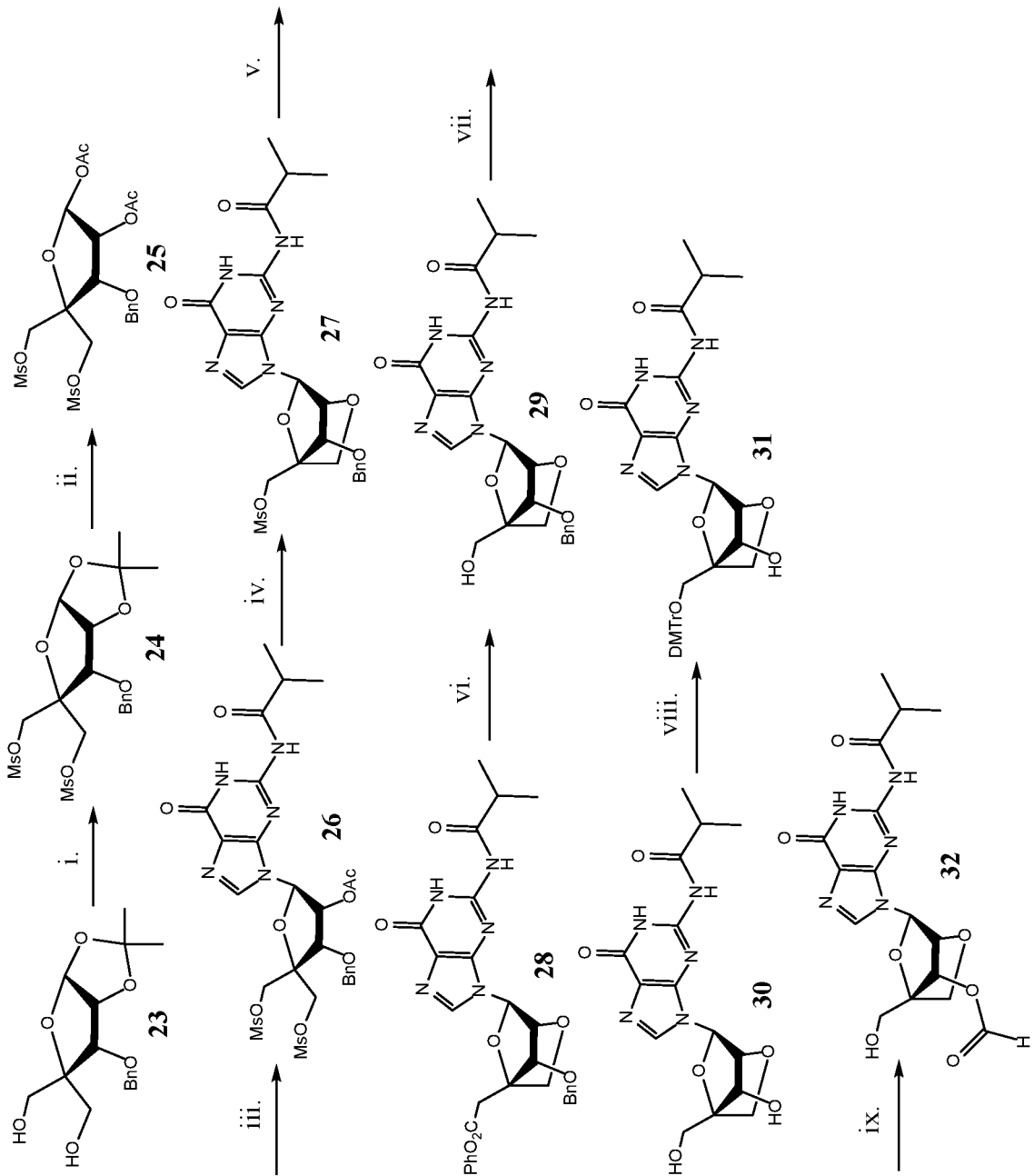
FIG. 10 shows multistep synthesis of 2'-O,4'-C-methylene-linked bicyclic guanine nucleotide (32) from (3aS,6aS)-6-(benzyloxy)-2,2-dimethyltetrahydrofuro[2,3-d][1,3]dioxole-5,5-diyl)dimethanol (23). First (i) the diol is reacted with MsCl to yield intermediate (24), which is hydrolyzed and acetylated (ii) to produce the two isomers of intermediate (25). This intermediate is fused (iii) with butyrated guanine to produce a guanine nucleotide (26) as a precursor (iv) to production of bicycle guanine nucleotide 27. The 5'OMs of bicyclic guanine 27 benzoylated (v) to produce benzoate-intermediate 28, and is then hydrolyzed (vi) to produce compound 29 having a free 5'OH. Intermediate 29 is further deprotected (vii) to obtain compound 30 with free 3' and 5' OH groups. The 5' OH group of compound 30 is blocked by DMTrCl (viii) to produce compound 31, which is acylated (viii) to produce the locked guanyl nucleotide (32).

2'-O,4'-C-methylene-linked bicyclic guanine nucleotide (compound 32, FIG. 10). The locked guanine nucleotide was synthesized according to the method shown in FIG. 10 starting with commercially available ((3aS,6aS)-6-(benzyloxy)-2,2-dimethyltetrahydrofuro[2,3-d][1,3]dioxole-5,5-diyl)dimethanol (compound 23) using the method of Koshkin, 2001, *J Org Chem,* 66:8504-12 (hereby incorporated by reference). The diol compound 23 in anhydrous pyridine was cooled in an ice bath and methanesulfonyl chloride (MsCl) is added. The mixture is stirred for 1 hour at room temperature, diluted with ethyl ether, and washed with water. The organic layer was dried (Na$_2$SO$_4$), concentrated under reduced pressure, co-evaporated with toluene, and dried in vacuo (FIG. 10, step i) to yield compound 24. A solution of this product in 80% trifluoroacetic acid was stirred at room temperature for one hour. The solvents were removed under pressure and the residue is dissolved in dichloromethane (DCM) and washed with saturated NaHCO$_3$ to yield compound 24.

Compound 24 was co-evaporated with anhydrous pyridine, dissolved in anhydrous pyridine, and treated with Ac$_2$O overnight. The reaction mixture was quenched by addition of saturated NaHCO$_3$ and washed with ethyl acetate. The organic layers were combined, washed with brine, dried, and concentrated under pressure (FIG. 10, step ii) to produce a mixture of two isomers of compound 25.

N,O-Bis(trimethylsilyl)acetamide (BSA) was added to a mixture of compound 25 and butyrated guanine in anhydrous acetonitrile. After refluxing for one hour, trimethylsilyl triflate is added and refluxing was continued further for 4 hours to produce a guanine nucleotide compound 26 (FIG. 10, step iii). The solution was cooled to room temperature, diluted with DCM, and washed with saturated NaHCO$_3$. The organic layer was dried, and concentrated under reduced pressure to obtain modified guanine nucleotide intermediate compound 26.

To a solution of the modified guanine nucleotide compound 26 in 1,4-dioxane/water (1:1, v:v) was added 2 M NaOH. After stirring 1 hour at room temperature, the reaction was diluted with saturated NaHCO$_3$ and extracted with DCM (FIG. 10, step iv) to produce the modified bicycle guanine nucleotide. The organic layers were dried and concentrated to obtain the bicyclic product compound 27.

Figure 14:
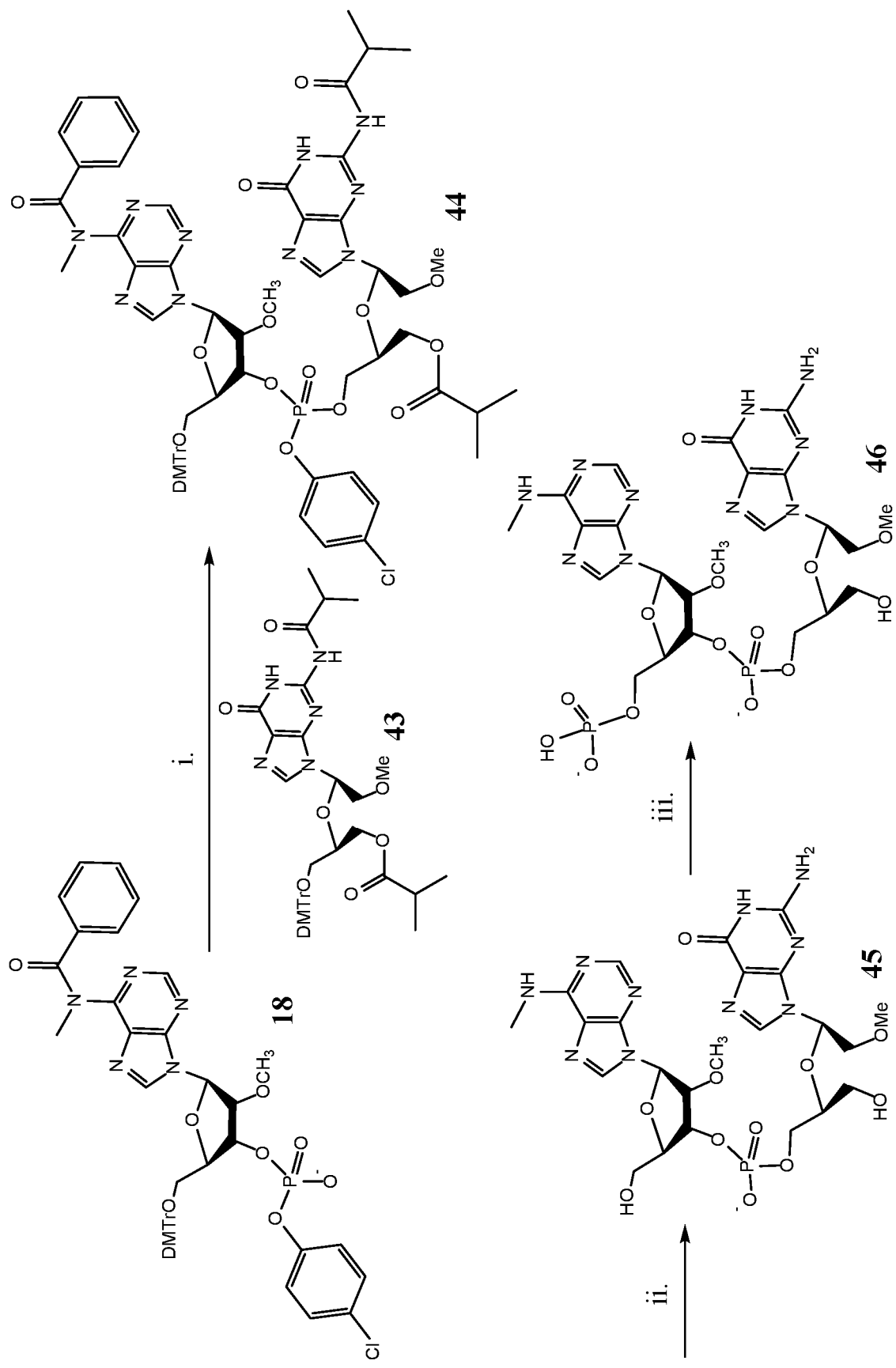
FIG. 14 shows synthesis of p-2'-OMe-m$^6$Ap-seco-2'-OMeG (46). Protected 2'OMeAp2'OMeG dinucleotide (44) is produced by combining 3'-p-2'-OMeA (18) with protected 2'-OMe secoguanosine (43) to produce intermediate 44 (i). The protective groups of intermediate 44 are removed (ii) to produce a 2'-OMeA-2'-OMeG dinucleotide (45). The 5'-hydroxy group of the adenosine group is phosphorylated (iii) to produce 2'-OMe-m$^6$Ap-seco-2'-OMeG 5'-monophosphate (46).

Compound 27 was reacted with sodium benzoate in anhydrous DMF and stirred for 5 hours at 100° C. (FIG. 14, step v). The mixture containing the 5'O-protected compound 28 was cooled, filtered, and suspended in ethyl acetate, washed with water, and dried.

H$_2$O and 2 M NaOH are added to a solution of compound 28 in 1,4-dioxane. The reaction mixture was refluxed for 24 hours, cooled to room temperature, and neutralized with acetic acid (FIG. 10, step vi) to produce compound 29 having a free 5'OH. Saturated NaHCO$_3$ was added, and the mixture was washed with DCM. Organic layers were combined, dried (Na$_2$SO$_4$), and concentrated under reduced pressure.

To a solution compound 29 in methanol was added 20% Pd(OH)$_2$/C, and HCO$_2$H. After refluxing the mixture for 10 min, the catalyst was filtered off and washed with methanol (FIG. 14, step vii). The combined filtrates were concentrated to obtain compound 30 with free 3' and 5' OH groups.

The 5' OH group of compound 30 was blocked as a DMTr ether according to the method of WO 99/14266 by preparing an anhydrous pyridine solution of the nucleotide, adding an excess of 4,4'-dimethoxytrityl chloride, stirring at room temperature for 2 hours, quenching the reaction with ice cold water, and extracting the product with DCM (FIG. 10, step viii). The combined organic phases were washed NaHCO$_3$-saturated water, brine, and dried Na$_2$SO$_4$ to give compound 31.

The 3'-OH group of the nucleotide 31 was blocked by an acyl group according to the method of WO 2009/124238 (hereby incorporated by reference). The 3' hydroxy group compound 31 was acylated with alkoyl chloride, triethylamine in DCM, followed by removal of the 5'O-DMTr group with hexafluoroisopropanol or aqueous acid to produce the locked guanyl nucleotide, compound 32 (FIG. 10, step viii).

Example 10

Figure 11:
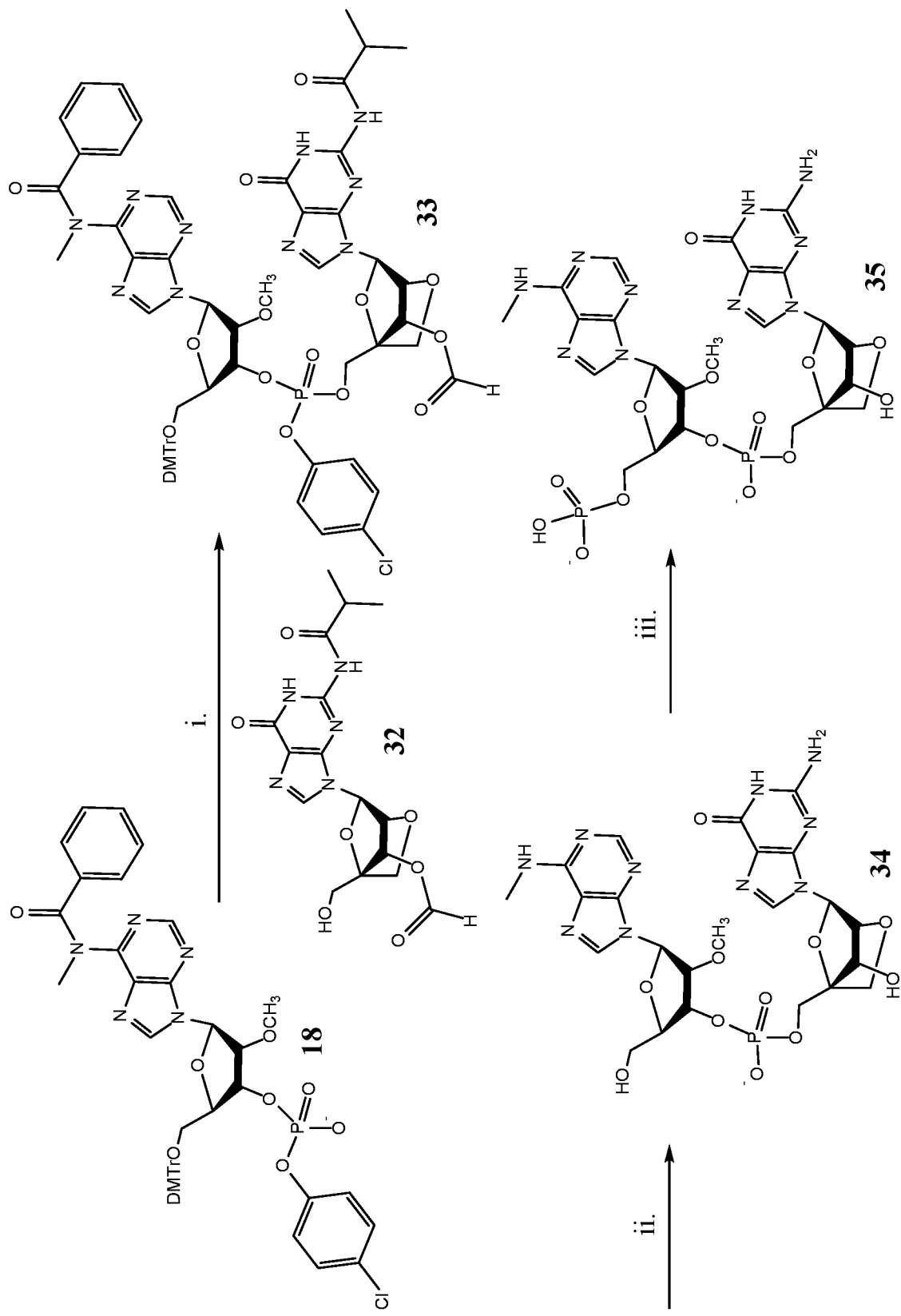
FIG. 11 shows synthesis of nucleotide m$^6$2'OMeAp-locked-2'OMeG (35) by (i) combining locked guanyl nucleotide (32) with benzoylated 3'-p-m$^6$2'-OMeA (18) to produce intermediate dinucleotide (33). The dinucleotide is deprotected (ii) to produce m$^6$2'OMeA-locked-2'-OMeG dinucleotide (34), which is phosphorylated (iii) to give 35.

Dinucleotide m$^6$2'OMeAp-locked-2'OMeG (compound 35, FIG. 11). The dinucleotide was produced by combining locked guanyl nucleotide, compound 32 (Example 9) with benzoylated 3'-p-m$^6$2'-OMeA compound 18 (Example 6) by the method of Lewdorowicz 2007. Locked guanyl compound 32 was mixed with 1 equivalent of benzoylated 3'-p-m$^6$2'-OMeA compound 18 in anhydrous acetonitrile and the mixture was dried by evaporation. A solution of 2,4,6,-triisopropylbenzenesulfonyl chloride and N-methylimidazole in acetonitrile was added and reacted for 4 hours to produce the protected m$^6$2'-OMeAp-locked-2'-OMeG dinucleotide compound 33 (FIG. 11, step i).

The protective groups of dinucleotide compound 33 were removed (FIG. 11, step ii) as described in Example 4 to produce m$^6$2'OMeA-locked-2'-OMeG dinucleotide compound 34. The 5'-hydroxy group of the adenosine group was phosphorylated according to the method of Lewdorowicz 2007 (FIG. 11, step iii). Phosphorus trichloride oxide in trimethyl phosphate was cooled to 4° C. and m$^6$2'OMeA-2'OMeG was added and stirred at 4° C. for 3 hours. Tetraethylammoniuum bromide (TEAB) was added to neutralize the mixture to produce the m$^6$2'-OMeAp-locked-2'-OMeG dinucleotide 5'-monophosphate (FIG. 11, compound 35).

Example 11

Figure 12:
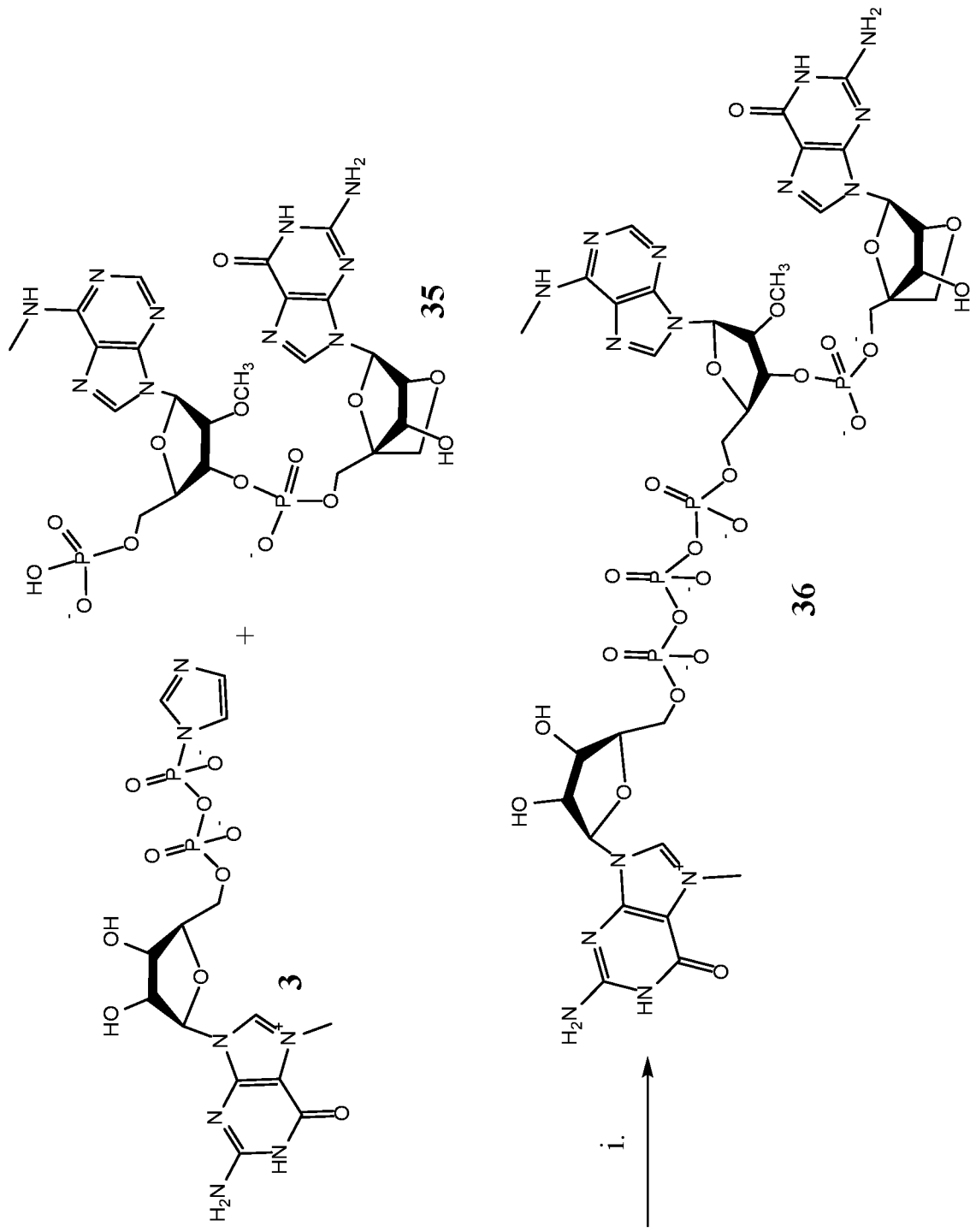
FIG. 12 shows synthesis of trinucleotide cap analog, m$^7$G(5')pppm$^6$2'OMeAp-locked-2'-OMeG (36) by combining the ammonium salt of m$^6$2'-OMeAp-locked-2'-OMeG dinucleotide 5'-monophosphate (35) with the sodium salt of m$^7$GDP-IM (3)

Trinucleotide cap analog, m$^7$G(5')ppp(5')m$^6$Amp-2'-O,4'-C-methylene-G (compound 36, FIG. 12). The trinucleotide cap analog is produced by the method described in Example 5. A mixture of ammonium salt of m$^6$2'-OMeAp-locked-2'-OMeG dinucleotide 5'-monophosphate (compound 35 produced in Example 10), four equivalents of a sodium salt of m$^7$GDP-IM (compound 3 produced in Example 1), and ZnCl$_2$ in DMF is stirred for 2 days at room temperature. The reaction is quenched by addition of water to yield m$^7$G(5')ppp(5')m$^6$Amp-2'-O,4'-C-methylene-G (compound 36).

Example 12

Figure 13:
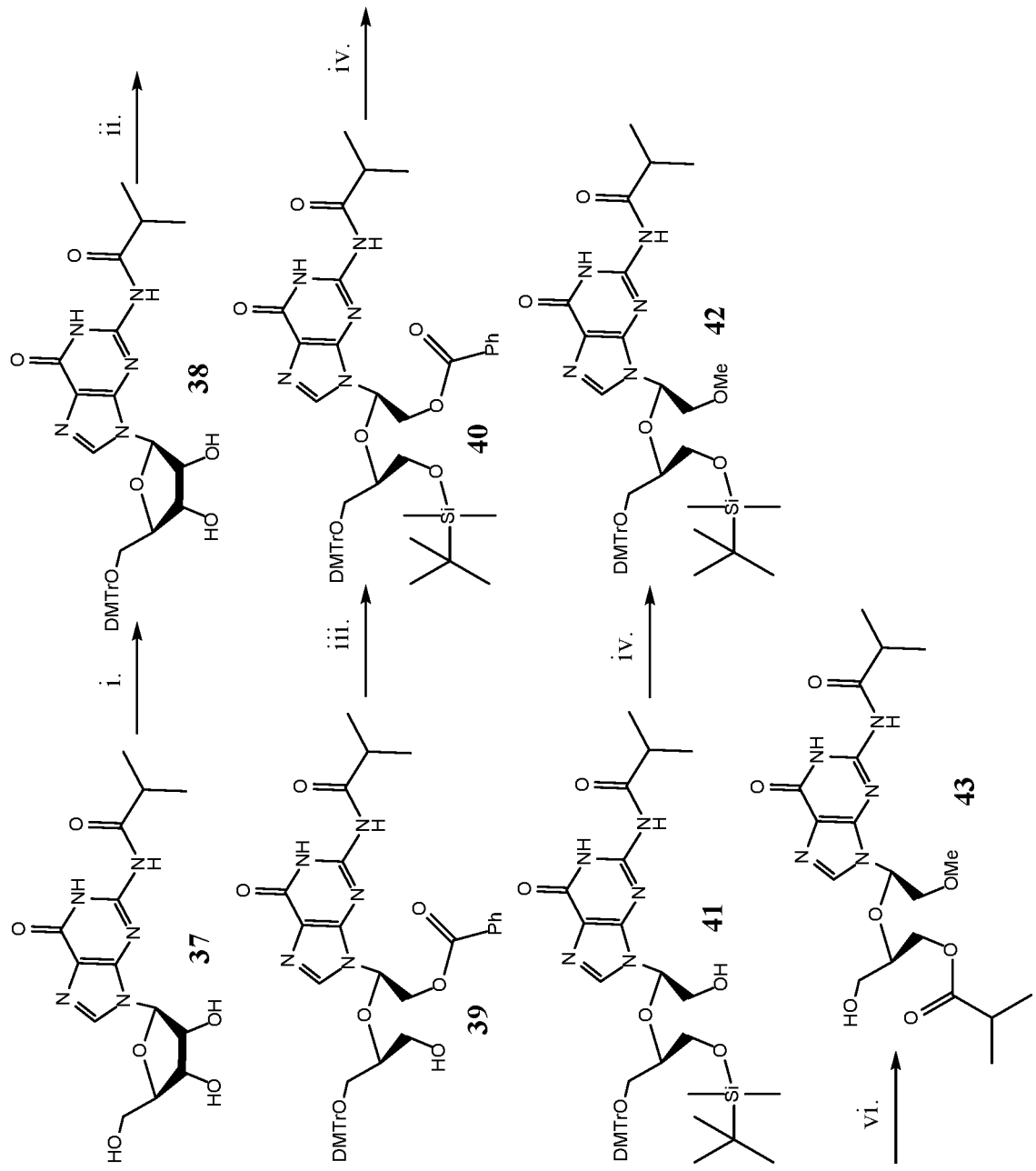
FIG. 13 shows synthesis of 2'OMe-seco-3'-O-isobutyryl, N$^2$-isobutyrylguanosine (43). The 5' OH group of N$^2$-isobutyrylguanosine (37) is blocked with DMTrCl to produce intermediate 38 (i), which is converted (ii) to an "unlocked" form, 2'-O-benzoylated secoguanine (39). The 3'-OH group of the 2'-O-benzoylated secoguanine is protected by TBDMSCl (40). The 2'-O-benzoyl group of intermediate 40 is removed (iv) to yield the free 2'-OH group (41), which is methylated (v) to yield intermediated 42. The silyl group is removed from the 3'-OH of intermediate 42 and the 3-OH group is butyrylated (v) to produce secoguanine (43) after deblocking of the 5'-ODMTr ether.

(R)-3-hydroxy-2-((R)-1-(2-isobutyramido-6-oxo-1,6-dihydro-9H-purin-9-yl)-2-methoxyethoxy)propyl isobutyrate (2'OMe-seco-3'-O-isobutyryl,N$^2$-isobutyrylguanosine; FIG. 13, compound 43). The 5' OH group of N$^2$-isobutyrylguanosine compound 37 was blocked by as a DMTr ether according to the method of WO 99/14266 by preparing a anhydrous pyridine solution of the nucleotide, adding an excess of 4,4'-dimethoxytrityl chloride, stirring at room temperature for 2 hours, quenching the reaction with ice cold water, and extracting the product (compound 38) with DCM (FIG. 13, step i). The combined organic phases were washed with NaHCO$_3$-saturated water, brine, and dried Na$_2$SO$_4$.

Guanosine compound 38 was converted to an "unlocked" form of compound 39 by the method of Landkjaer, 2009, *Biorg Med Chem*, 17:5420-25 (hereby incorporated by reference). The DMTr guanosine compound 38 was dissolved in a stirred mixture of dioxane and water. To this mixture was added NaIO$_4$ dissolved in water, stirred for one hour, and further dioxane is added. The suspension was filtered and the filter cake was washed with dioxane. The filtrates were combined and sodium borohydride was added and the mixture stirred for 30 minutes (FIG. 17, step ii). The mixture was neutralized by addition of pyridine:acetic acid buffer. After evaporation, DCM is added and the mixture was washed with saturated aqueous NaHCO$_3$. The organic phase was separated and evaporated to dryness under reduced pressure, to yield 5'O-DMT-2',3'-secoguanine.

2'-O-benzoyl-5'-O-DMT-2',3'-secoguanine compound 39 was prepared from 5'O-DMT-2',3'-secoguanine by the method of Landkjaer 2009. The nucleotide was co-evaporated with anhydrous toluene and dried for 12 hours in vacuo. The residue was dissolved at room temperature in anhydrous mixture of DCM with pyridine and cooled to −78° C. Benzoyl chloride was added over 15 minutes with stirring for 1 hour at −78° C. The mixture was warmed to room temperature, and ethanol was added and the mixture was washed with saturated aqueous NaHCO$_3$ and the separated aqueous phase was back-extracted with DCE. The organic phases were combined and evaporated to dryness to yield the 2'-O-benzoylated secoguanine compound 39 (FIG. 13, step ii).

The 3'-OH group of the the 2'-O-benzoylated secoguanine was protected by TBDMSCl according to the method of Perlikova 2014, *ChemBioChem*, 15:146-156 (hereby incorporated by reference) (FIG. 13, step iii) to yield compound 40.

The 2'-O-benzoyl group compound 40 was removed by the method of Nishino, 1985, *Tetrahedron*, 41:5503-06 (hereby incorporated by reference) using a suspension of sodium methoxide in THF for 1 hour at room temperature (FIG. 13, step iv). The reaction was quenched by neutralization to yield the free 2'-OH group of compound 41.

The 2'-OH group of compound 41 was methylated by reaction with NaH and methyl iodide in THF at 0° C. (step v) to yield compound 42. The silyl group was removed from the 3'-OH group with nBu$_4$NF by the method of Perlikova 2014 and the 3'-OH group was butyrlated (step v) to produce the secoguanine compound 43 after removal of the DMTr protecting group with acid (CF$_3$CO$_2$H, step vi).

Example 13

((2R,3S,4S,5R)-3-((((S)-2-((R)-1-(2-amino-6-oxo-1,6-dihydro-9H-purin-9-yl)-2-methoxyethoxy)-3-hydroxypropoxy)(hydroxy)phosphoryl)oxy)-4-methoxy-5-(6-(methylamino)-9H-purin-9-yl)tetrahydrofuran-2-yl)methyl hydrogen phosphate (p-2'-OMe-m$^6$Ap-seco-2'-OMeG, FIG. 14, compound 46). Protected 2'OMeAp2'OMeG dinucleotide, compound 44 (FIG. 14) was produced by combining 3'-p-2'-OMeA compound 18 (Example 6) with protected 2'-OMe secoguanosine compound 43 (Example 12) by the method of Lewdorowicz 2007. First, 3'-p-2'-OMeA compound 18 was mixed with an equivalent of 2'OMe guanosine compound 43 in anhydrous acetonitrile and the mixture was dried by evaporation. A solution of 2,4,6,-triisopropylbenzenesulfonyl chloride and N-methylimidazole in acetonitrile was added and the mixture was reacted for 4 hours to produce compound 44 (FIG. 14, step i).

The protective groups of compound 44 were removed (step ii, using reactions described in Example 4, FIG. 5, step i), to produce a 2'-OMeA-2'-OMeG dinucleotide compound 45. The 5'-hydroxy group of the adenosine group was phosphorylated according to the method of Lewdorowicz 2007 (FIG. 14, step iii). Phosphorus trichloride oxide in trimethyl phosphate was cooled to 4° C. and the 5'-O-guanine-adenine dinucleotide-3'-O compound 45 was added and stirred at 4° C. for 3 hours. Tetraethylammoniuum bromide (TEAB) was added to neutralize the mixture to produce 2'-OMe-m$^6$Ap-seco-2'-OMeG 5'-monophosphate, compound 46.

Example 14

Figure 15:
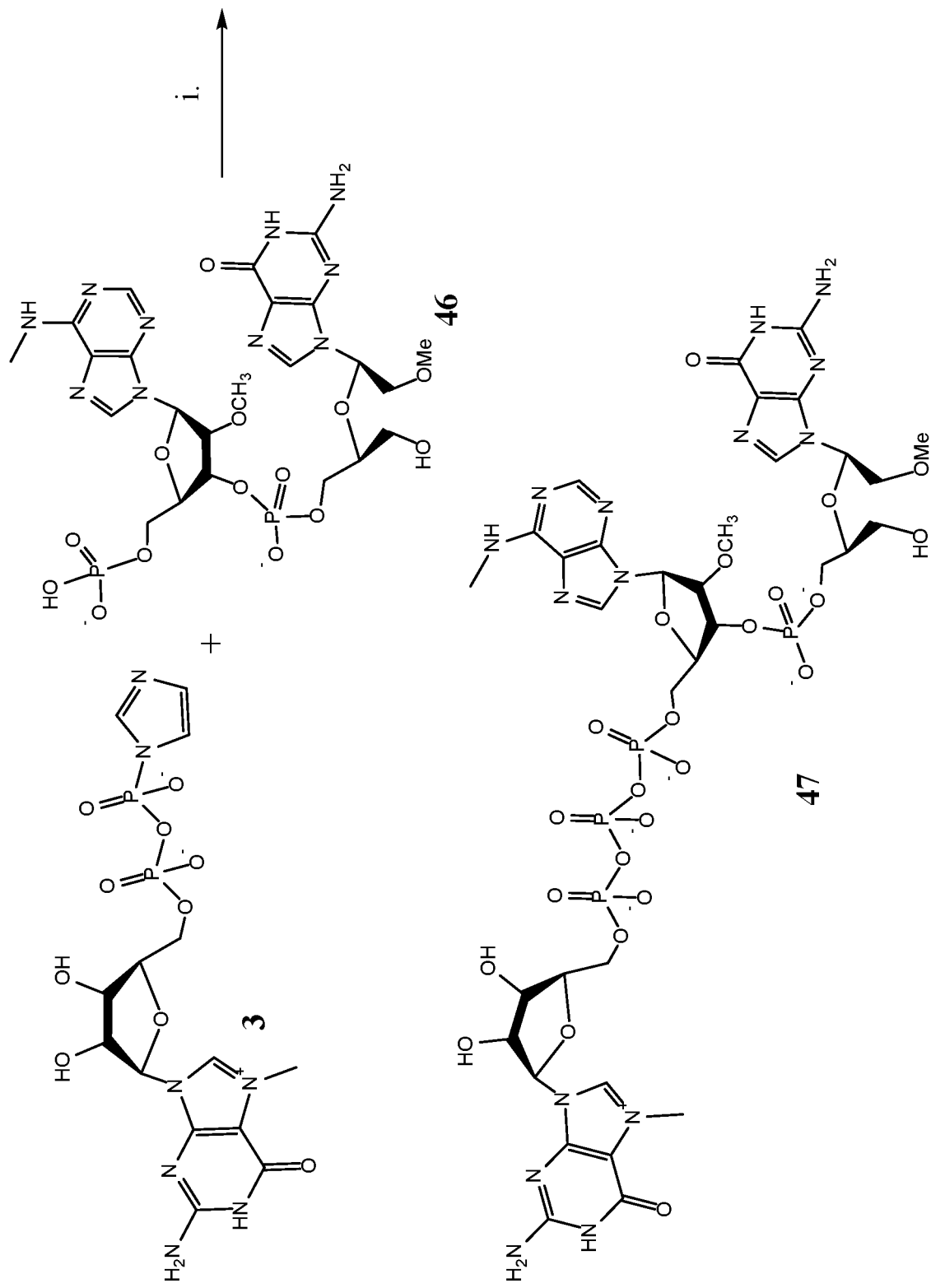
FIG. 15 shows synthesis of trinucleotide cap analog, m$^7$G(5')pppm$^6$2'-OMeAp-seco-2'-OMeG (47) from ammonium salt of 2'-OMe-m$^6$Ap-seco-2'-OMeG 5'-monophosphate (46) and the sodium salt of m$^7$GDP-IM (3).

Trinucleotide cap analog, m$^7$G(5')ppp(5')m$^6$Amp-seco-2'-OMeG (compound 47, FIG. 15). The trinucleotide cap analog is produced by the method described in Example 8. A mixture of ammonium salt of 2'-OMe-m$^6$Ap-seco-2'-OMeG 5'-monophosphate, compound 46 (produced in Example 13 ), four equivalents of a sodium salt of m$^7$GDP-IM (compound 1 produced in Example 1), and ZnCl$_2$ in DMF is stirred for 2 days at room temperature. The reaction is quenched by addition of water to yield m$^7$G(5')ppp(5') m$^6$Amp-seco-2'-OMeG (compound 47).

Example 15

(2R,3S,4S,5R)-2-(hydroxymethyl)-5-(2-isobutyramido-6-oxo-1,6-dihydro-9H-purin-9-yl)tetrahydrofuran-3,4-diyl bis(2-methylpropanoate) (2'-O-isobutyryl-3'O-isobutyryl, N$^2$-isobutyrylguanosine, compound 50) is synthesized from commercially available guanosine (compound 48) by the method of Wolf, 2008, *Org Biomol Chem*, 6:899-907 (hereby incorporated by reference). First, guanosine is isobutyrated at the N$^2$ position and crystallized from water to give N$^2$-isobutyrylguanosine, and the 5'-hydroxy group is protected with a DMTr group according to the method of WO 99/14266 to yield compound 49. Second, 2'- and 3' hydroxy groups are subject to isobutyrylation, and the DMTr group is removed by treatment with 5% trichloroacteic acid to produce 2'-O-isobutyryl,3'-O-isobutyryl,N$^2$-isobutyrylguanosine, compound 50.

Example 16

((2R,3S,4S,5R)-3-(((((2R,3R,4S,5R)-5-(2-amino-6-oxo-1,6-dihydro-9H-purin-9-yl)-3,4-dihydroxytetrahydrofuran-2-yl)methoxy)oxidophosphoryl)oxy)-5-(6-amino-9H-purin-9-yl)-4-methoxytetrahydrofuran-2-yl)methyl hydrogen phosphate (p-2'-OMe-ApG, compound 53). To synthesize p-2'-OMe-ApG, compound 6 (5'O-DMT-2'O-Me-N$^6$benzoyl-AMP-PhCl, Example 2) is combined with isobutyrated guanosine compound 50 (Example 15) by the method of Lewdorowicz 2007. Compound 6 is mixed with an equivalent of isobutyrated guanosine compound 50 in anhydrous acetonitrile. The mixture is dried by evaporation. A solution of 2,4,6,-triisopropylbenzenesulfonyl chloride and N-methylimidazole in acetonitrile is added and the mixture is reacted for 4 hours to produce the protected 2'-OMe-ApG dinucleotide compound 51.

The protective groups of 2'-OMeApG dinucleotide compound 51 are removed using known reactions, e.g., by a method selected from Lewdorowicz 2007; Huss, 1988, *J Org Chem,* 53:499-506; Zhou, 1986, *Tetrahedron,* 42:4149-56; Reese, 1986, *Tetrahedron Letters,* 27:2291-94; Abramova, 2008, *Biorg Med Chem,* 16:9127-32; Abramova, 2013, *Beilstein J Org Chem,* 9:2898-909; Hashmi, 1994, *Nucleotides & Nucleotides,* 13:1059-67; Hsu, 1985, *Nucleotides & Nucleotides,* 4:377-89; Puech, 1988, *J Med Chem,* 31:1897-907 (hereby incorporated by reference) to produce 2'-OMe-ApG dinucleotide (compound 52). The 5'-hydroxy group of compound 52 is phosphorylated according to the method of Lewdorowicz 2007 (step ii). Phosphorus trichloride oxide in trimethyl phosphate is cooled to 4° C. and the 5'-O-guanine-adenine dinucleotide-3'-O intermediate is added and stirred at 4° C. for 3 hours. Tetraethylammoniuum bromide (TEAB) is added to neutralize the mixture to produce p-2'-OMe-ApG dinucleotide (compound 53).

Example 17

Trinucleotide cap analog, $m^7G(5')ppp$-2'OMeApG (compound 54). The trinucleotide cap analog is produced by the method of Lewdorowicz 2007. A mixture of ammonium salt of pApG (compound 53 produced in Example 16), four equivalents of a sodium salt of $m^7GDP$-IM (compound 3 produced in Example 1), and $ZnCl_2$ in DMF is stirred for 2 days at room temperature. The reaction is quenched by addition of water to yield $m^7G(5')ppp$-2'OMeApG (compound 54).

Example 18

In Vitro Transcription Reaction:

For ARCA and ARC CAP1 mRNAs, in vitro transcription was performed using the standard protocol (see Table, below). All of components were mixed, and T7 RNA polymerase (E2040 from NEB) was added in the reaction mixture. The transcription reaction was incubated for 2 hrs at 37 C. After 2 hrs of reaction time, DNASEI (NEB) and buffer were added to the transcription reaction and incubated for 15 mins at 37 C. The crude of reaction mix was purified using RNA purification kit (Macherey-Nagel).

| Transcription Component | | Amount to |
|---|---|---|
| Component Type | Name | add (ul) |
| Water | Water | up to 200 uL |
| rNTPs | rATP (100 mM) | 10 |
| | rCTP (100 mM) | 10 |
| | rN1MPU (100 mM) | 10 |
| | rGTP (100 mM) | 10 |
| | ARCA* or ARC CAP1** (100 mM) | 10 |
| 10X rxn buffer | 10x rxn buffer | 20 |
| Template | Linear Plasmid | 10 ug |
| Enzymes | RNase Inhibitor (40 U/uL) | 5 |
| | Inorganic Pyrophosphatase (0.1 U/uL) | 4 |
| | T7 Mix | 8 |

*ARCA, 3'-OMe-$m^7G(5')p_3G$ (Trilink)
**ARC CAP 1, $m^7G(5')p_3AmpG$

For Vaccinia mRNA, in vitro transcription was performed using the standard protocol without ARCA or ARC CAP1. All of components were mixed, and T7 RNA polymerase (E2040 from NEB) was added in the reaction mixture. The transcription reaction was incubated for 2 hrs at 37 C. After 2 hrs of reaction time, DNASEI (NEB) and buffer were added to the transcription reaction and incubated for 15 mins at 37 C. The crude of reaction mix was purified using RNA purification kit (Macherey-Nagel). The RNA was denatured at 65° C. for 5 min and then snap chilled to relieve any secondary conformations. For the total 1 mL capping reaction, 1 mg denatured RNA in 700 μL of nuclease-free water was used along with 100 μL 1 (10×) capping buffer, 50 μL (10 mM) GTP, 50 μL (4 mM) SAM, 50 μL of (10 units/μL) Vaccinia capping enzyme, and 50 μL of mRNAcap2'-O-methyltransferase at (50 units/μL) were combined and incubated at 37° C. for 1 h. The mixture capped mRNA was purified using RNA purification kit (Macherey-Nagel).

Figure 16:
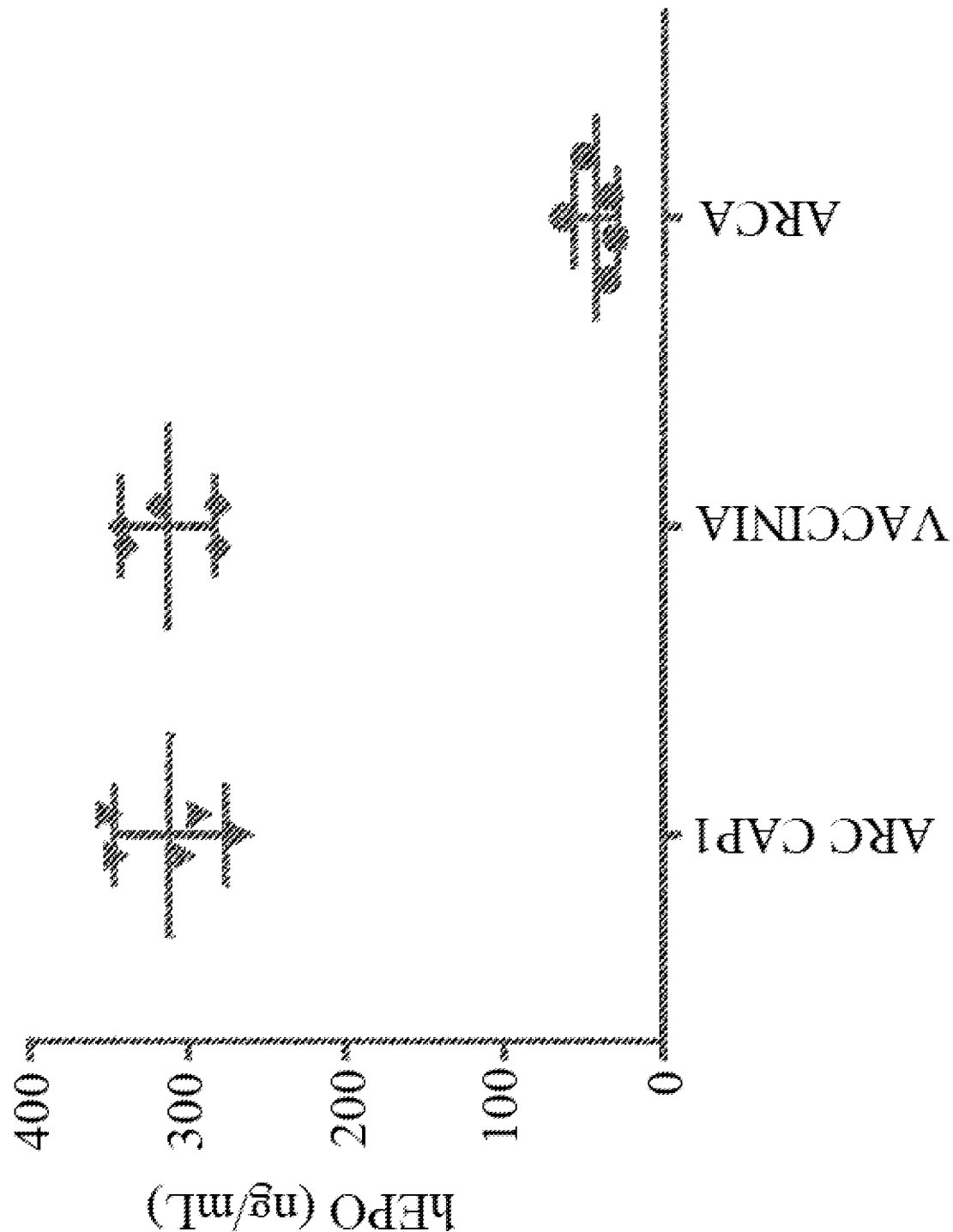
FIG. 16 shows expression of m$^7$G(5')ppp-RNA transcribed from ARC CAP1 (m$^7$G(5')p$_3$AmpG); ARCA (3'-OMe-m$^7$G(5')p$_3$G); or VACCINIA, without ARC CAP1 or ARCA, by post-transcriptional capping by a vaccinia capping enzyme.

$m^7G(5')p_3$-RNA were delivered 0.3 mg/kg i.v. into 12-16 weeks old male mice. Blood samples were collected at 6 hours post dose, and plasma was isolated. Protein expression was performed using ELISA (e.bioscience). Results are shown in FIG. 16.

The results show that the efficiency of transcription using trinucleotide analog ARC CAP1 is substantially improved compared to dinucleotide ARCA. This is because the amount of protein expression for ARC CAP1 is greater than ARCA, and because vaccinia-mediated capping produces $m^7G(5')p_3$-RNA that results in comparable protein expression compared to ARC CAP1. ARC CAP1-RNA is just as efficient translated as enzymatically capped RNA.

Although the present disclosure is described with respect to certain embodiments and examples, various modifications may be made without departing from the spirit and scope of the invention.

What is claimed is as follows:

1. A compound of formula $m^7G(5')p_3(5')N_1pN_2$, wherein
    $m^7G$ is a ribonucleotide consisting of $N^7$-methylguanine and a ribose or a modified ribose, wherein one or both of the 2' or 3' carbons of the modified ribose has a fluoro or a C1-C6 alkoxy substituent;
    $(5')p_3(5')$ is a 5' to 5' triphosphate linkage, wherein the triphosphate linkage may be substituted with one or more phosphorothioate groups;
    $N_1$ is a ribonucleotide comprising a seco (UNA) ribose optionally substituted at the 2' or 3' carbons with one or more fluoro or C1-C6 alkoxy substituents, and a base selected from the group consisting of adenine, uridine, guanine, cytosine, $N^6$-methyladenine, $N^1$-methyladenine, pseudouracil, $N^1$-methylpseudouracil, 5-iodouracil, 4-thiouracil, 2-thiouracil, 5-methyluracil, pseudoisocytosine, 5-methoxycytosine, 2-thiocytosine, 5-hydroxycytosine, $N^4$-methylcytosine, 5-hydroxymethylcytosine, hypoxanthine, $N^1$-methylguanine, $O^6$-methylguanine, $N^2$-methylguanine ($m^2G$), $N^2,N^2$-dimethylguanine ($m^{2,2}G$), $N^2,N^7$-dimethylguanine ($m^{2,7}G$), and isoguanine; and
    $N_2$ is a ribonucleotide consisting of (i) a base selected from the group consisting of adenine, uridine, guanine, cytosine, $N^6$-methyladenine, $N^1$-methyladenine, pseudouruacil, $N^1$-methylpseudouracil, 5-iodouracil, 4-thiouracil, 2-thiouracil, 5-methyluracil, pseudoisocytosine, 5-methoxycytosine, 2-thiocytosine, 5-hydroxycytosine, $N^4$-methylcytosine, 5-hydroxymethylcytosine, hypoxanthine, $N^1$-methylguanine, $O^6$-methylguanine, $N^2$-methylguanine ($m^2G$), $N^2,N^2$-dimethylguanine ($m^{2,2}G$), $N^2,N^7$-dimethylguanine ($m^{2,7}G$), and isoguanine; and (ii) a ribose moiety comprising a ribose or a modified ribose, wherein one or both of the 2' or 3' carbons of the modified ribose has a fluoro or a C1-C6 alkoxy substituent;

wherein the m$^7$G ribonucleotide is linked at its 5'-OH to the triphosphate bridge, the triphosphate bridge is linked to a 5'-OH of the N$_1$ ribonucleotide, the N$_1$ nucleotide is linked via its 3'-OH to a phosphate, p, and the phosphate is linked to a 5'-OH of the N$_2$ ribonucleotide;

or a salt or solvated form thereof.

2. The compound of claim 1, wherein the base of N$_1$ is adenine, uridine, guanine, or cytosine.

3. The compound of claim 2, wherein the base of N$_1$ is adenine.

4. The compound of claim 2, wherein one or both of the 2' or 3' carbons of the seco (UNA) ribose of N$_1$ has a fluoro or a C1-C6 alkoxy substituent.

5. The compound of claim 2, wherein the 2' carbon of the seco (UNA) ribose of N$_1$ has a fluoro or a C1-C6 alkoxy substituent.

6. The compound of claim 2, wherein the 2' carbon of the seco (UNA) ribose of N$_1$ has a C1-C6 alkoxy substituent.

7. The compound of claim 2, wherein the 2' carbon of the seco (UNA) ribose of N$_1$ has a methoxy substituent.

8. The compound of claim 1, wherein the base of N$_2$ is selected from the group consisting of guanine, N$^1$-methylguanine, O$^6$-methylguanine, m$^2$G, m$^{2,7}$G, and isoguanine.

9. The compound of claim 8, wherein the base of N$_2$ is guanine, N$^1$-methylguanine, O$^6$-methylguanine, or isoguanine.

10. The compound of claim 8, wherein the base of N$_2$ is guanine.

11. The compound of claim 1, wherein the 2' carbon of at least one of m$^7$G, N$_1$, or N$_2$ ribonucleotide is substituted by a C1-C6-alkoxy.

12. The compound of claim 1, wherein at least one ribose of the N$_1$ or N$_2$ ribonucleotide is substituted by a 2'-O-methyl.

13. The compound of claim 1, wherein the triphosphate bridge consists of 1, 2, or 3 phosphorothioate groups.

14. The compound of claim 1, wherein the compound is m$^7$G(5')p$_3$-seco-2'-OMeApG, wherein seco-2'-OMeA is 2'-O-methyladenosine-seco(UNA)ribose and G is guanosine.

15. The compound of claim 1, wherein the compound increases the efficiency of m$^7$G(5')p$_3$-RNA produced by in vitro transcription compared to 3'-OMe-m$^7$G(5')p$_3$G.

16. The compound of claim 15, wherein in vitro transcription is mediated by T7 RNA polymerase or T6 RNA polymerase.

17. A compound of formula m$^7$G(5')p$_3$(5')N$_1$pN$_2$, wherein m$^7$G is a ribonucleotide consisting of N$^7$-methylguanine and a ribose or a ribose analog selected from the group consisting bicyclic (LNA) ribose, seco (UNA) ribose, or a modified ribose wherein one or both of the ribose 2' or 3' carbons has a fluoro or a C1-C6 alkoxy substituent;

wherein (5')p$_3$(5') is a 5' to 5' triphosphate linkage, and wherein N$_1$ and N$_2$ are ribonucleotides, wherein one or both of N$_1$ and N$_2$ consists of a nucleobase independently selected from the group consisting of andenine, N$^6$-methyladenine, N$^1$-methyladenine, uracil, pseudouruacil, N$^1$-methylpseudouracil, 5-iodouracil, 4-thiouracil, 2-thiouracil, 5-methyluracil, cytosine, pseudoisocytosine, 5-methoxycytosine, 2-thiocytosine, 5-hydroxycytosine, N$^4$-methylcytosine, 5-hydroxymethylcytosine, hypoxanthine, guanine, N$^1$-methylguanine, O$^6$-methylguanine, 1-methyl-guanosine, N$^2$-methyl-guanosine (m$^2$G), N$^2$,N$^2$-dimethyl-guanosine (m$^{2,2}$G), 2-methyl-2'-O-methyl-guanosine (m$^2$Gm), N$^2$,N$^2$-dimethyl-2'-O-methyl-guanosine (m$^{2,2}$Gm), 1-methyl-2'-O-methyl-guanosine, N$^2$,N$^7$-dimethyl-2'-O-methyl-guanosine (m$^{2,7}$Gm), and isoguanine; and a ribose or ribose analog, wherein one or both N$_1$ and N$_2$ consist of a ribose analog selected from the group consisting of LNA, UNA and modified UNA wherein one or both of the UNA 2' or 3' carbons has a fluoro or a C1-C6 alkoxy substituent, wherein either N$_1$ or N$_2$ but not both consist of a ribose analog or a modified ribose wherein one or both of the ribose 2' or 3' carbons has a fluoro or a C1-C6 alkoxy substituent; and wherein the m$^7$G ribonucleotide is linked at its 5'-OH to the triphosphate bridge, wherein the triphosphate bridge is linked to a 5'-OH of the N$_1$ ribonucleotide, wherein N$_1$ nucleotide is linked via its 3'-OH to a phosphate, p, wherein the phosphate is linked to a 5'-OH of the N$_2$ ribonucleotide;

or a salt or solvated form thereof.

18. The compound of claim 17, wherein m$^7$G is a ribonucleotide consisting of N$^7$-methylguanine and a ribose, wherein (5')p$_3$(5') is a 5' to 5' triphosphate linkage, wherein N$_1$ is a ribonucleotide consisting of a nucleobase selected from adenine, and a ribose analog selected from the group consisting of LNA, UNA and modified UNA wherein one or both of the UNA 2' or 3' carbons has a fluoro or a C1-C6 alkoxy substituent;

wherein N$_2$ is a ribonucleotide consisting of a nucleobase selected from guanine and a ribose or a ribose analog selected from the group consisting of LNA, UNA and modified UNA wherein one or both of the UNA 2' or 3' carbons has a fluoro or a C1-C6 alkoxy substituent; and wherein the m$^7$G ribonucleotide is linked at its 5'-OH to the triphosphate bridge, wherein the triphosphate bridge is linked to a 5'-OH of the N$_1$ ribonucleotide, wherein N$_1$ nucleotide is linked via its 3'-OH to a phosphate, p, wherein the phosphate is linked to a 5'-OH of the N$_2$ ribonucleotide;

or a salt or solvated form thereof.

* * * * *